United States Patent
Ito

(10) Patent No.: US 10,274,992 B2
(45) Date of Patent: Apr. 30, 2019

(54) WEARABLE DEVICE WITH MUSCLE ACTIVITY DETECTOR

(71) Applicant: KYOCERA Corporation, Kyoto-shi, Kyoto (JP)

(72) Inventor: Shingo Ito, Kawasaki (JP)

(73) Assignee: KYOCERA CORPORATION, Kyoto (JP)

( * ) Notice: Subject to any disclaimer, the term of this patent is extended or adjusted under 35 U.S.C. 154(b) by 71 days.

(21) Appl. No.: 15/526,026

(22) PCT Filed: Nov. 11, 2015

(86) PCT No.: PCT/JP2015/081795
§ 371 (c)(1),
(2) Date: May 11, 2017

(87) PCT Pub. No.: WO2016/076376
PCT Pub. Date: May 19, 2016

(65) Prior Publication Data
US 2017/0308118 A1    Oct. 26, 2017

(30) Foreign Application Priority Data
Nov. 12, 2014    (JP) ................................ 2014-230057

(51) Int. Cl.
*G06F 3/01*    (2006.01)
*G06F 1/16*    (2006.01)
(Continued)

(52) U.S. Cl.
CPC ............ *G06F 1/163* (2013.01); *A61B 5/0488* (2013.01); *G06F 3/011* (2013.01); *G06F 3/014* (2013.01);
(Continued)

(58) Field of Classification Search
CPC .......... G06F 1/163; G06F 3/011; G06F 3/014; G06F 3/017; G06F 3/0482; G06F 3/04883; A61B 5/0488
See application file for complete search history.

(56) References Cited

U.S. PATENT DOCUMENTS

2004/0243342 A1    12/2004    Rekimoto
2013/0321261 A1*   12/2013    Nakasu ................... G06F 3/017
                                                                    345/156
(Continued)

FOREIGN PATENT DOCUMENTS

JP    7-248873 A    9/1995
JP    11-338597 A   12/1999
(Continued)

OTHER PUBLICATIONS

International Search Report in PCT/JP2015/081795, dated Dec. 22, 2015.

*Primary Examiner* — Lisa S Landis
(74) *Attorney, Agent, or Firm* — Hauptman Ham, LLP

(57) ABSTRACT

A wearable device can be attached to a particular bodily part of a user. For example, the wearable device can be strapped to one upper limb from among the left and right upper limbs of the user. The wearable device includes a display configured to display images; a muscle activity detector coming in contact with the concerned upper limb, the muscle activity detector configured to detect muscle activity of the concerned upper limb; and a controller configured to detect a bodily motion of the concerned upper limb based on the detected muscle activity, and configured to make the display to perform a predetermined display operation in response to the bodily motion.

5 Claims, 16 Drawing Sheets

| PATTERN | BODILY PART | TYPE OF MOTION |
|---|---|---|
| 1 | FINGER | BENDING OF EACH FINGER |
| 2 | | EXTENSION OF EACH FINGER |
| 3 | | PINCHING BETWEEN FIRST FINGER AND ONE OF SECOND TO FIFTH FINGERS |
| 4 | | CLENCHING |
| 5 | | UNCLENCHING |
| 6 | HAND (WRIST) | PALMAR FLEXION |
| 7 | | DORSAL FLEXION |
| 8 | | RADIAL FLEXION |
| 9 | | ULNAR FLEXION |
| 10 | FOREARM | PRONATION |
| 11 | | SUPINATION |
| 12 | UPPER LIMB | NEUTRAL POSITION |

(51) Int. Cl.
*A61B 5/0488* (2006.01)
*G06F 3/0482* (2013.01)
*G06F 3/0488* (2013.01)

(52) U.S. Cl.
CPC ............ *G06F 3/017* (2013.01); *G06F 3/0482* (2013.01); *G06F 3/04883* (2013.01); *G06F 2203/0381* (2013.01)

(56) References Cited

U.S. PATENT DOCUMENTS

| | | | |
|---|---|---|---|
| 2015/0061842 A1* | 3/2015 | Yoon | G04G 21/04 340/12.5 |
| 2015/0101423 A1* | 4/2015 | Tuli | G01P 13/00 73/865.4 |
| 2015/0161371 A1 | 6/2015 | Hoshi et al. | |

FOREIGN PATENT DOCUMENTS

| | | |
|---|---|---|
| JP | 2002-287869 A | 10/2002 |
| JP | 2002-358149 A | 12/2002 |
| JP | 2006-171412 A | 6/2006 |
| JP | 2010-246636 A | 11/2010 |
| JP | 2013-172447 A | 9/2013 |
| JP | 2013-250637 A | 12/2013 |
| JP | 2014-102838 A | 6/2014 |
| JP | 2014-170280 A | 9/2014 |
| WO | 2014/147713 A1 | 9/2014 |

\* cited by examiner

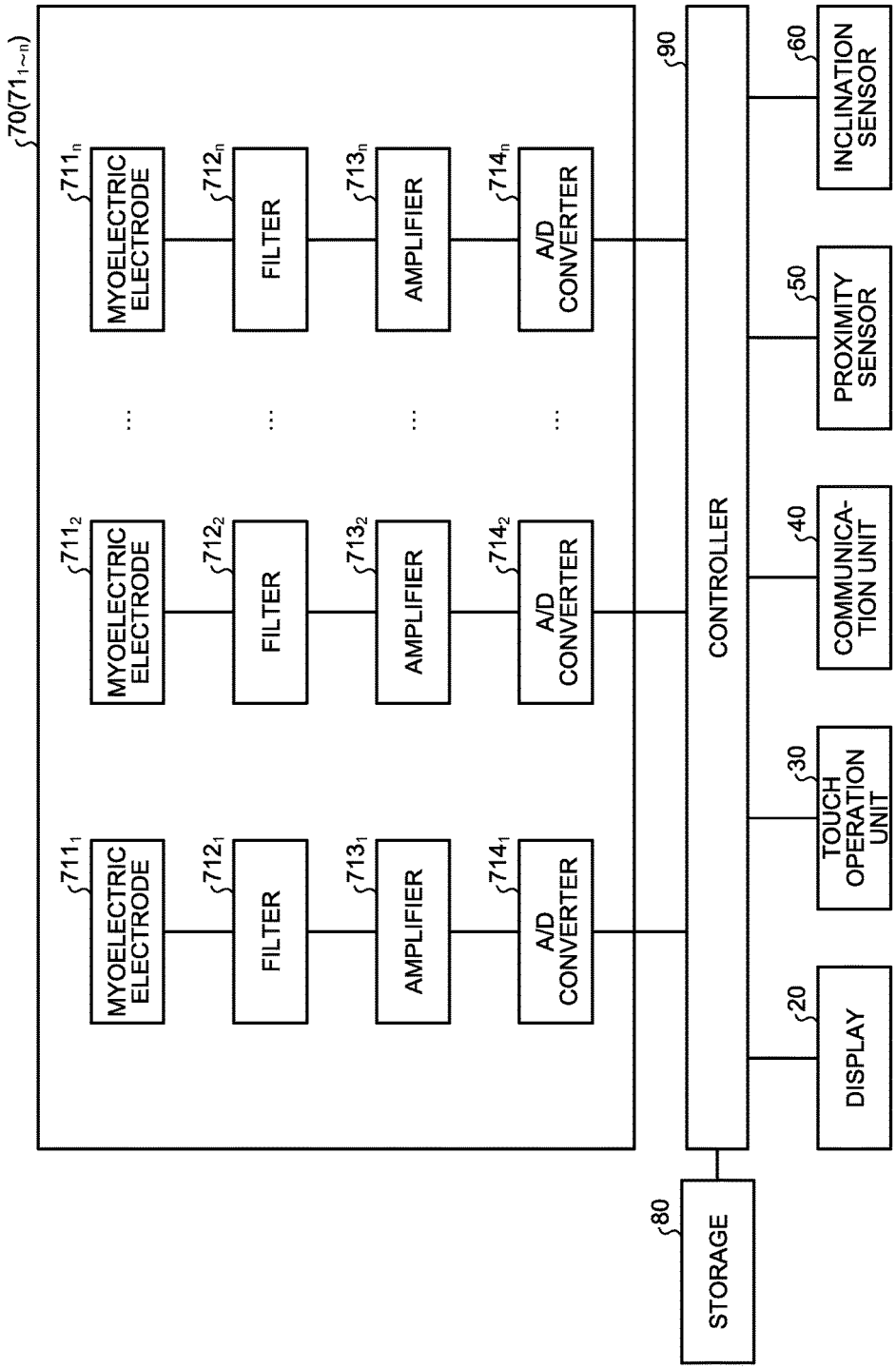

FIG.3

| PATTERN | BODILY PART | TYPE OF MOTION |
|---|---|---|
| 1 | FINGER | BENDING OF EACH FINGER |
| 2 | | EXTENSION OF EACH FINGER |
| 3 | | PINCHING BETWEEN FIRST FINGER AND ONE OF SECOND TO FIFTH FINGERS |
| 4 | | CLENCHING |
| 5 | | UNCLENCHING |
| 6 | HAND (WRIST) | PALMAR FLEXION |
| 7 | | DORSAL FLEXION |
| 8 | | RADIAL FLEXION |
| 9 | | ULNAR FLEXION |
| 10 | FOREARM | PRONATION |
| 11 | | SUPINATION |
| 12 | UPPER LIMB | NEUTRAL POSITION |

WEARABLE DEVICE WITH MUSCLE ACTIVITY DETECTOR

RELATED APPLICATIONS

The present application is a National Phase of International Application Number PCT/JP2015/081795, filed Nov. 11, 2015, which claims priority to Japanese Application Number 2014-230057, filed Nov. 12, 2014.

FIELD

The present invention relates to a wearable device that can be attached to a particular bodily part of a user.

BACKGROUND

As the wearable device mentioned above, in recent years, a wearable electronic device is known that is modeled on a wristwatch and that can be strapped to the wrist of one arm from among the left and right arms of the user and can be operated using motions of the hand or the fingers of the other arm. For example, it has been mentioned that a wearable electronic device has a touch-sensitive area provided therein so that predetermined operations can be performed by touching the touch-sensitive area with a finger of the other hand.

SUMMARY

A wearable device according to one aspect that is attached to one upper limb from among left and right upper limbs of a user includes a display configured to display an image, a muscle activity detector coming in contact with the one upper limb, the muscle activity detector configured to detect muscle activity of the one upper limb, and a controller configured to detect a bodily motion of the one upper limb based on the detected muscle activity, and configured to make the display to perform a predetermined display operation in response to the bodily motion.

A wearable device according to one aspect that is attached to body of a user includes a display configured to display an image, and a controller configured to detect motion of a bodily part, excluding a bodily part to which the wearable device is attached, that is not capable of coming in contact with the wearable device, and make the display to perform a predetermined display operation in response to the detected bodily motion.

BRIEF DESCRIPTION OF DRAWINGS

FIG. 2 is a diagram illustrating an example of the functional blocks of the wearable device according to the embodiments.

FIG. 3 is a diagram illustrating the types of bodily motions detected by a controller.

DESCRIPTION OF EMBODIMENTS

In the wearable electronic device, there are only a limited modes of input done using motions of the hand or the fingers of the arm, from among the left and right arms, to which the wearable electronic device has been strapped. Hence, there is a demand for enabling implementation of more diverse operations. It is an object of the present invention to provide a wearable device that enables implementation of diverse operations. Embodiments of the present invention are described below in detail with reference to the accompanying drawings. However, the present invention is not limited by the explanation given below. The constituent elements mentioned in the following explanation include constituent elements that may easily occur to one skilled in the art, constituent elements that are substantially same as the inventions, and constituent elements that are what is called an equivalent scope.

Figure 1A:
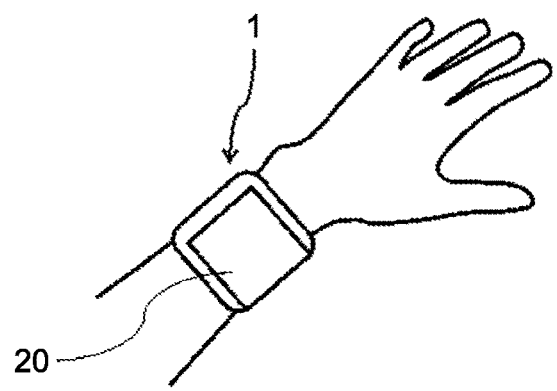
FIG. 1A is a diagram illustrating an exemplary overall configuration of a wearable device according to embodiments.
Figure 1B:
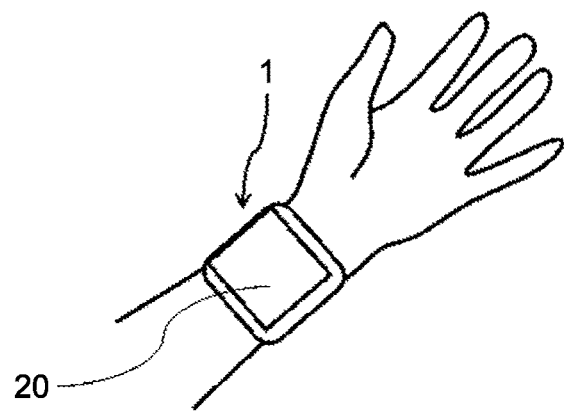
FIG. 1B is a diagram illustrating an exemplary overall configuration of the wearable device according to the embodiments.

FIG. 1A is a diagram illustrating an exemplary overall configuration of a wearable device 1 according to the embodiments. FIG. 1B is a diagram illustrating an exemplary overall configuration of the wearable device according to the embodiments. In FIGS. 1A and 1B, it is illustrated that the wearable device 1 is strapped to one upper limb from among the left and right upper limbs of the user. In the present description, an upper limb represents a arm, a hand, and fingers of a person; and is assumed to include an upper arm, a forearm, a hand, and fingers. In the embodiments, as an example, as illustrated in FIGS. 1A and 1B, the explanation is given under the assumption that the wearable device 1 is strapped to the left forearm, which is the forearm of the left upper limb of the user. In FIG. 1A is illustrated the side of the back of the hand. In FIG. 1B is illustrated the side of the flat of the hand.

The wearable device 1 is, for example, of the wristband type or the wristwatch type. The wearable device 1 is strapped in a detachably attachable manner to an upper limb of a user. The majority of the wearable device 1 is made of, for example, a material having flexibility and elasticity. As a result, the wearable device 1 remains attached firmly to the upper limb of the user.

The wearable device 1 includes a display 20 at such a position in the wearable device 1 which is visible to the user. The display 20 is laterally placed on the wearable device 1. Moreover, the display module 20 is placed along the arm of the concerned upper limb of the user.

The display 20 includes a display area in the portion corresponding to the side of the back of the hand in the forearm of the user, and includes a display area in the portion corresponding to the side of the flat of the hand in the forearm of the user. The display 20 is, for example, a display such as a liquid crystal display (LCD) or an organic EL (Organic Electro-Luminescence) display. Herein, the display 20 can be a curved display having a portion in the curved surface shape, or can be a flexible display that is flexible in nature.

Explained below with reference to FIG. 2 are the functions of the wearable device 1 according to the embodiments. FIG. 2 is a diagram illustrating an example of the functional blocks of the wearable device 1 according to the embodiments. As illustrated in FIG. 2, the wearable device 1 according to the embodiments includes the display 20, a touch operation unit 30, a communication unit 40, a proximity sensor 50, an inclination sensor 60, a muscle activity detector 70, a storage 80, and a controller 90.

The display 20 displays videos or images under the control of the controller 90.

The touch operation unit 30 detects an input attributed to a user operation. The touch operation unit 30 represents, for example, one or more buttons disposed in the wearable device 1. When a button is pressed, the touch operation unit 30 outputs a predetermined signal to the controller 90. Meanwhile, the touch operation unit 30 can be, for example, a touch sensor that is disposed in the wearable device 1 and that detects a touch. The touch sensor can be disposed in an overlapping manner with the display 20. In that case, the touch operation unit 30 detects, as the input position, such a position on the display surface at which a finger of the user has touched, and outputs a signal corresponding to the detected input position to the controller 90. In the touch sensor, it is possible to use a touch panel of various types such as an electrostatic capacitance touch panel, an ultrasonic touch panel, a pressure-sensitive touch panel, a resistive touch panel, or an optical detection touch panel.

In the case in which a touch sensor is used as the touch operation unit 30, the user touches the display surface with fingers and performs various touch operations. Examples of the types of touch operation include an operation in which the display surface is touched with a finger and then the finger is lifted within a short time (a tap operation), an operation of flipping the display surface with a finger in an arbitrary direction (a flick operation), and an operation of touching the display surface with a finger and then moving the display surface while keeping the finger on it (a slide operation).

The communication unit 40 includes an antenna and an RF circuit. Under the control of the controller 90, the communication unit 40 performs, for example, communication including information communication or telephone communication with an external device so as to send and receive a variety of information. In the case of performing wireless communication, for example, the communication unit 40 can implement a communication method of short-range wireless communication in which the communication distance is in the range of few centimeters to one meter or in the range of few meters to a few tens of meters. Examples of short-range wireless communication include Bluetooth (registered trademark), ZigBee (registered trademark), infrared communication, visible light communication, and NFC (Near Field Communication). For example, in the case in which the aim is to go through the automatic ticket gate of a railway station by communicating with the automatic ticket gate using the wearable device 1, the communication unit 40 can implement NFC as the communication method. At that time, the configuration can be such that, when the wearable device 1 strapped to an upper limb is held over the information reader of the automatic ticket gate, the communication unit 40 establishes communication between the automatic ticket gate and the wearable device 1.

Alternatively, the communication unit 40 can implement some other communication method such as the communication method in which communication is performed via a public line network. Examples of the communication method for performing communication via a public line network include LTE (Long Term Evolution) and W-CDMA (Wideband Code Division Multiple Access). Meanwhile, the communication unit 40 can alternatively be configured to perform wired communication.

The proximity sensor 50 detects that an object has come close to the wearable device 1. In the proximity sensor 50, for example, it is possible to use a combination of an infrared LED representing a light emitting element and a photodiode representing a light receiving element. From the variation in the output of photodiode, the proximity sensor 50 calculates the distance to an object, such as a finger of the other upper limb of the user, coming close to the proximity sensor 50. More particularly, the infrared LED emits infrared light and the proximity sensor 50 receives the infrared light reflected from the finger. For example, when the proximity sensor 50 is away from the finger of the user, the infrared light emitted by the infrared LED is not received by the photodiode. However, for example, when the proximity sensor 50 comes close to a finger of the user, the infrared light emitted by the infrared LED reflects from the finger and is received by the photodiode. In this way, depending on whether or not the proximity sensor 50 has come close to a finger of the user, there is variation in the amount of infrared light received by the photodiode. The proximity sensor 50 outputs, to the controller 90, the amount of infrared light received by the photodiode. Based on the amount of infrared light received, the controller 90 detects the proximity of the object. Meanwhile, the proximity sensor 50 is not limited to be an infrared sensor, and alternatively can be an electrostatic capacitance sensor, for example.

The inclination sensor 60 detects, for example, the inclination of the display surface of the display 20 with respect to the horizontal plane. For example, the inclination sensor 60 is a triaxial acceleration sensor of the semiconductor type. The acceleration sensor outputs, to the controller 90, triaxial (X, Y, and Z) acceleration data for the display surface of the display 20. Herein, the direction toward one end of the display surface of the display 20 is assumed to be the X-axis direction, the direction orthogonal to the X-axis direction within the display surface is assumed to be the Y-axis direction, and the direction orthogonal to the X-axis direction and the Y-axis direction is assumed to be the Z-axis direction. The X-Y plane including the X axis and the Y axis are parallel to the display surface. Moreover, the X-axis direction, the Y-axis direction, and the Z-axis direction of the display surface of the display 20 are coincident with the X-axis direction, the Y-axis direction, and the Z-axis direction, respectively, of the wearable device 1.

The muscle activity detector 70 comes in contact with the skin of the user and detects the muscle activity of the upper limb of the user. Herein, the muscle activity detector 70 is represented by myoelectric potential detectors 71 that detect, as the muscle activity, the electric potential generated on the body surface due to muscle contraction. The myoelectric potential detectors 71 come in contact with the skin of the user, and detect myoelectric potential signals generated on the surface of the skin due to a bodily motion of the user. Then, the myoelectric potential detectors 71 output the detected myoelectric potential signals to the controller 90. Herein, a plurality of myoelectric potential detectors 71 is disposed on the inner periphery of the wearable device 1.

Each of a plurality of myoelectric potential detectors 71 (711, 712, . . . , 71$n$) includes a plurality of myoelectric electrodes 711 (711$_1$, 711$_2$, . . . , 711$_n$), a plurality of filters 712 (712$_1$, 712$_2$, . . . , 712$_n$), a plurality of amplifiers 713 (713$_1$, 713$_2$, . . . , 713$_n$), and a plurality of A/D converters 714 (714$_1$, 714$_2$, . . . , 714$_n$).

When the wearable device 1 is strapped to an upper limb of the user, the myoelectric electrodes 711 abut against the skin of the user. Then, the myoelectric electrodes 711 detect the surface potential generated on the surface of the skin of the user as myoelectric potential signals.

As the filters 712, it is possible to use, for example, bandpass filters having the passband in the range of a few tens of Hz to 1.5 kHz. The filters 712 remove the polarization voltage of the myoelectric electrodes 711, remove the noise of the power source, and remove the high-frequency noise. Moreover, the filters 712 remove the abovementioned noise from the myoelectric potential signals output from the myoelectric electrodes 711, and output traversable signals to the amplifiers 713.

The amplifiers 713 amplify the myoelectric potential signals, which are output from the filters 712, to a level at which signal analysis becomes possible. The amplified myoelectric potential signals are output to the A/D converters 714.

The A/D converters 714 convert the myoelectric potential signals, which are analog signals output from the amplifiers 713, into digital signals. The digital signals obtained by conversion of the A/D converters 714 are then output to the controller 90.

The myoelectric potential detectors 71 representing the muscle activity detector 70 can further include an integrator in addition to the configuration explained above. The integrator performs integration firstly by rectifying, using a full-wave rectifier circuit, either the myoelectric potential signals filtered by the filters 712 or the myoelectric potential signals amplified by the amplifiers 713, and then by performing smoothing using a smoothing filter. Then, the integrator outputs an integrated myoelectric potential signal, which represents the myoelectric potential signals subjected to integration, to the A/D converters 714.

The storage 80 is a memory device such as a nonvolatile memory device or a readable-writable memory device. Examples of a nonvolatile memory device include a nonvolatile semiconductor memory such as a ROM (Read Only Memory), and a hard disk drive. Examples of a readable-writable memory device include an SRAM (Static Random Access Memory) and a DRAM (Dynamic Random Access Memory). The storage 80 is used to store various codes. Moreover, the storage 80 is used to store a plurality of bodily motion detection patterns in which the frequency characteristic of myoelectric potential data (described later) and various bodily motions are separately associated. Furthermore, the storage 80 is used to store display operation patterns each of which is associated with one of a plurality of bodily motion detection patterns.

The controller 90 is configured with, for example, at least one micro processing unit (MPU). The controller 90 follows the procedure instructed in software and implements various operations in the wearable device 1. The controller 90 sequentially reads the operation code from various codes, such as an operating system and application codes, and implements the operations. In this way, the controller 90 controls the operations of various constituent elements. The controller 90 outputs the data required by each constituent element, such as control signals or image signals required for displaying videos or images on the display 20.

From the variation in the output of the photodiode of the proximity sensor 50, the controller 90 calculates the distance to an object coming close to the wearable device 1, such as the distance to a finger of the other upper limb of the user. Moreover, based on the amount of infrared light received by the photodiode of the proximity sensor 50, the controller 90 detects the proximity of an object.

The controller 90 detects the variation in the triaxial acceleration data of the inclination sensor 60, and determines the movement of the display surface of the display 20 or the movement of the wearable device 1. The controller 90 implements a trigonometric function with respect to the gravitational acceleration detected by the acceleration sensor, and calculates the angle of inclination of the display surface of the display 20 or the wearable device 1 with respect to the horizontal plane. If there is a change in the angle of inclination of the display surface of the display 20 or the wearable device 1 with respect to the horizontal plane, then the controller 90 instructs the display 20 to perform a predetermined display operation based on the inclination angle at that time.

The controller 90 analyzes the myoelectric potential data output from the myoelectric potential detectors 71 representing the muscle activity detector 70, and detects the bodily motion of the user.

The controller 90 samples the myoelectric potential signals representing digitalized myoelectric potential data, and performs frequency transform with respect to the sampled myoelectric potential data according to various methods such as FFT (Fast Fourier Transform) or wavelet transform.

Then, based on frequency data obtained as a result of frequency transform, the controller 90 detects the type of bodily motion of the user from the frequency characteristic obtained by analyzing the frequency spectrum.

Typically, the frequency characteristic of myoelectric potential data differs according to the type of bodily motion of a person. Thus, if the frequency characteristic of myoelectric potential data and the types of bodily motions are associated and stored in advance, the controller 90 determines the bodily motion of the user based on the frequency data derived from the myoelectric potential data. Hence, the controller 90 refers to the bodily motion detection patterns stored in the storage 80, and detects the type of bodily motion of the user from the frequency characteristic of myoelectric potential data. Herein, for example, a neural network can be used in determining the bodily motion.

The controller 90 refers to the display operation patterns stored in the storage 80 and performs control so as to make the display 20 to perform a display operation corresponding to the detected bodily motion.

As a result of having the configuration described above, the controller 90 detects the bodily motion of the upper limb of the user based on the muscle activity that is detected using the myoelectric potential detected by the myoelectric potential detectors 71 of the muscle activity detector 70; and makes the display 20 to perform a predetermined display operation in response to the detected bodily motion.

Moreover, based on the integrated myoelectric potential signal output from the integrator, for example, the controller 90 detects muscular tension according to integration average value (IEMG: Integrated ElectroMyoGraphy). The integrated myoelectric potential signal has a proportional relationship to the muscular tension on the whole. Thus, based on whether or not the detected muscular tension has exceeded a predetermined threshold value, the controller 90 can determine whether or not the user has actually performed a predetermined bodily motion such as a clenching motion (described later) or a power motion (described later).

As far as the indicator for detecting a bodily motion from myoelectric potential data is concerned, other than using the frequency spectrum or the integration average value explained earlier, it is possible to use various indicators such as the mean power frequency (MPF), the central frequency, or the effective value (RMS: Root Mean Square), or the standard deviation of the frequency distribution (SDFD: Standard Deviation of Frequency Distribution).

Meanwhile, the muscles responsible for the motions of an upper limb of the person are separately present in that upper limb. For example, the muscles responsible for various motions of the forearm, the hand, and the fingers of an upper limb are separately present in the forearm region. For that reason, if it becomes possible for the controller 90 to measure, at a sufficient resolution, the myoelectric potential signals or the myoelectric potential distribution occurring due to the movement of the muscles responsible for various motions of the hand or the fingers; then the controller 90 can determine the motion of the forearm, the hand, or the fingers.

For example, regarding the index finger, the middle finger, the ring finger, and the little finger representing the second finger to the fifth finger, respectively; the controller 90 determines the motion of each finger by measuring the myoelectric potential of such regions which correspond to the motions of that finger and which are present in the deep flexor muscle of fingers, the superficial flexor muscle of fingers, and the common digital extensor muscle representing the muscles of the forearm region responsible for the motions of the fingers. The deep flexor muscle of fingers is particularly responsible for the bending motion of the first joint of the second to fifth fingers; the superficial flexor muscle of fingers is particularly responsible for the bending motion of the second joint of the second to fifth fingers; and the common digital extensor muscle is particularly responsible for the extension motion of the second to fifth fingers. Moreover, the controller 90 measures the myoelectric potential of the long flexor muscle of thumb representing the muscle in the forearm region responsible for the motions of the pollex or the thumb representing the first finger; and thus determines the motions of all of the first to fifth fingers. Hence, for example, in order to determine the motions of the first to fifth fingers, it is preferable that the myoelectric electrodes 711 are located immediately above the deep flexor muscle of fingers, the superficial flexor muscle of fingers, the common digital extensor muscle, and the long flexor muscle of thumb. In that case, it is preferable that the wearable device 1 includes four myoelectric potential detectors 71 corresponding to the four myoelectric electrodes 711. Meanwhile, regarding the locations at which the myoelectric electrodes 711 are to be placed in contact with the body, other than placing them above the muscles mentioned above, it is also preferable to place the myoelectric electrodes 711 at positions at which the myoelectric potential of the muscles responsible for the target motions for detection can be detected. For example, a method can be implemented in which a plurality of myoelectric electrodes 711 are installed in the wearable device 1 and the most suitable myoelectric potential detection positions are narrowed down. The number of myoelectric electrodes is assumed to be equal to the allocatable count on the inner periphery of the wearable device 1. Other than such a method, any conventional method can be implemented by which it becomes possible to determine the type of bodily motion of each finger, the hand, or the arm of an upper limb.

Given below is the explanation about the types of bodily motions detected by the controller 90. FIG. 3 is a diagram illustrating the types of bodily motions detected by the controller 90. Herein, regarding the bodily motion of an upper limb as detected by the wearable device 1 according to the embodiments, the subjects are classified into fingers, the hand, and the forearm, for example.

Firstly, regarding the motions of the fingers, the explanation is given about the bending motion of each of the first to fifth fingers (first pattern), the extension motion of each finger (second pattern), the pinching motion between the first finger and one of the second to fifth fingers (third pattern), the clenching motion of a hand (fourth pattern), and the unclenching motion of a hand (fifth pattern). Regarding the muscles responsible for the bodily motions of the fingers as given in the first to fifth patterns, the explanation is given earlier. The controller 90 detects the myoelectric potential generated due to the movement of those muscles and detects the bodily motions according to the first to fifth patterns.

The "bending motion of each finger (first pattern)" includes, for example, a bodily motion of bending the third joint, which is the third joint from the tip of the finger or which is the joint at the base of the finger, of any one of the second to fourth fingers. Moreover, the "bending motion of each finger (first pattern)" includes, for example, a bodily motion of bending the first joint, which is the first joint from the tip of the finger, as well as bending the second joint, which is the second joint from the tip of the finger, of any one of the second to fourth fingers. Furthermore, the "bending motion of each finger (first pattern)" includes, for example, a bodily motion of bending all of the first to third joints of any one of the second to fourth fingers. Moreover, the "bending motion of each finger (first pattern)" includes the motion of simultaneously bending a plurality of fingers from among the first to fifth fingers.

Furthermore, the "bending motion of each finger (first pattern)" also includes, for example, a bodily motion of moving the second finger in the crosswise direction with the joint at the base of the second finger serving as the pivot point. Herein, the crosswise direction implies the direction of getting close to the third finger and moving away from the third finger.

The "extension motion of each finger (second pattern)" represents the opposite motion to the bending motion of each finger (first pattern). For example, in the "extension motion of each finger (second pattern)", the state in which none of the first to third joints of a finger, from among the second to fourth fingers, is bent can be considered as "the state in which the concerned finger is extended". The "extension motion of each finger (second pattern)" includes a bodily motion for attaining "the state in which a finger is extended".

Meanwhile, the state in which a joint of a finger is bent by an angle greater than a predetermined angle can be considered as "the state in which the finger is bent"; and the state in which a joint of a finger is bent by an angle smaller than the predetermined angle can be considered as "the state in which the finger is extended". In this case, the predetermined angle can be appropriately set. Regarding the method for estimating the angle of bending of each joint of a finger, it is possible to implement the method disclosed in Japanese Patent Application Laid-open No. 2010-125287 A.

In the "pinching motion between the first finger and one of the second to fifth fingers (third pattern)", the characteristics of the myoelectric potential signals detected based on the concerned bodily motion are distinguished from the characteristics of the myoelectric potential signals detected based on the motion of simply bending a finger. The concerned bodily motion occurs due to a user-intended motion. For that reason, for example, if the user bends a finger all of a sudden, it does not result in false detection of the bending as the concerned bodily motion. As a result, the "pinching motion between the first finger and one of the second to fifth fingers (third pattern)" is suitable to be assigned for a type of operation performed in response to a bodily motion.

More specifically, when a motion of "pinching between the first finger and one of the second to fifth fingers" is performed, the first finger and one of the second to fifth fingers exert force on each other. For that reason, the user becomes able to perceive the fact of performing a motion, thereby becoming able to easily recognize that an input is actually performed.

The "clenching motion of a hand (fourth pattern)" is, for example, a motion for forming a fist. The "clenching motion of a hand (fourth pattern)" is the bodily motion of bending all of the first to fifth fingers during the bending motion of each finger (first pattern). Thus, although there is partial overlapping with the bending motion of each finger (first pattern), the "clenching motion of a hand (fourth pattern)" is classified as a separate pattern in order to simply the following explanation about the display modes. The muscles responsible for the concerned bodily motion are identical to the muscles responsible for the finger motions described earlier. Hence, the controller 90 detects the myoelectric potential generated due to the movement of those muscles, and detects a clenching motion of the hand.

The "unclenching motion of a hand (fifth pattern)" represents the opposite motion to the clenching motion of a hand (fourth pattern). The "unclenching motion of a hand (fifth pattern)" is, for example, a bodily motion for attaining the state in which no joints of the first to fifth fingers are bent. Thus, although there is partial overlapping with the extension motion of each finger (second pattern), the "unclenching motion of a hand (fifth pattern)" is classified as a separate pattern in order to simply the following explanation about the display modes.

Meanwhile, the state in which the joints of the first to fifth fingers are bent by an angle greater than a predetermined angle can be considered as "the state in which the hand is clenched"; and the state in which the joints of the first to fifth fingers are bent by an angle smaller than a predetermined angle can be considered as "the state in which the hand is unclenched". In this case, the predetermined angle can be appropriately set.

The following explanation is given about hand motions such as the palmar flexion of a hand (sixth pattern), the dorsal flexion of a hand (seventh pattern), the radial flexion of a wrist (eighth pattern), and the ulnar flexion of a wrist (ninth pattern).

The "palmar flexion of a hand (sixth pattern)" is a bodily motion of bending the wrist to the side of the flat of the hand. For example, the muscles responsible for this bodily motion include the radial flexor muscle of wrist, the long palmar muscle, and the ulnar flexor muscle of wrist. Hence, the controller 90 detects the myoelectric potential generated due to the movement of one of those muscles, and detects the palmar flexion of a hand.

The "dorsal flexion of a hand (seventh pattern)" is a bodily motion of bending the wrist to the side of the back of the hand. Thus, the "dorsal flexion of a hand (seventh pattern)" is the opposite motion to the palmar flexion of a hand (sixth pattern). For example, the muscles responsible for this bodily motion include the long radial extensor muscle of wrist, the short radial extensor muscle of wrist, and the ulnar extensor muscle of wrist. Hence, the controller 90 detects the myoelectric potential generated due to the movement of one of those muscles, and detects the dorsal flexion of a hand.

The "radial flexion of a wrist (eighth pattern)" is a bodily motion of bending the wrist joint to the side of the pollex representing the side of the radius constituting the forearm. For example, if the wearable device 1 is strapped to the left upper limb with the side of the back of the hand of the left forearm representing the upper side and with the side of the flat of the hand of the left forearm representing the lower side, then the radial flexion of the wrist is same as bending the wrist to the right-hand side. For example, the muscles responsible for this bodily motion include the long radial extensor muscle of wrist and the short radial extensor muscle of wrist. Hence, the controller 90 detects the myoelectric potential generated due to the movement of one of those muscles, and detects the radial flexion of a hand.

The "ulnar flexion of a wrist (ninth pattern)" is a bodily motion of bending the wrist joint to the side of the ulna constituting the forearm (to the side of the little finger). Thus, the "ulnar flexion of a wrist (ninth pattern)" represents the opposite motion to the radial flexion of a wrist (eighth pattern). For example, if the wearable device 1 is strapped to the left upper limb with the side of the back of the hand of the left forearm representing the upper side and with the side of the flat of the hand of the left forearm representing the lower side, then the ulnar flexion of the wrist is same as bending the wrist to the left-hand side. For example, the muscles responsible for this bodily motion include the long ulnar flexor muscle of wrist and the ulnar extensor muscle of wrist. Hence, the controller 90 detects the myoelectric potential generated due to the movement of one of those muscles, and detects the ulnar flexion of a wrist.

The following explanation is given about forearm motions such as the pronation of a forearm (10-th pattern) and the supination of a forearm (11-th pattern).

The "pronation of a forearm (10-th pattern)" is a bodily motion for turning a forearm in such a way that the back of the hand faces the side of the face of the user. In the case of the left upper limb, for example, the "pronation of a forearm (10-th pattern)" is a motion for turning the left forearm in the clockwise direction around a virtual line joining the left elbow and the left wrist of the left forearm. The controller 90 detects the myoelectric potential or the muscular tension generated due to the movement of the muscles responsible for this bodily motion, and detects the pronation of the forearm. For example, in the left upper limb, if the amount of rotation in the clockwise direction is greater than a predetermined value, then the controller 90 can determine that pronation has been performed. The amount of rotation in a rotation of a forearm can be calculated based on the variation in the frequency characteristic of myoelectric potential data or the variation in the muscular tension according to the bodily motion.

The "supination of a forearm (11-th pattern)" is a bodily motion for turning a forearm in such a way that the flat of the hand faces the side of the face of the user. The "supination of a forearm (11-th pattern)" represents the opposite movement to the "pronation of a forearm (10-th pattern)". In the case of the left upper limb, for example, the "supination of a forearm (11-th pattern)" is a motion for turning the left forearm in the counterclockwise direction around the left forearm. The controller 90 detects the myoelectric potential or the muscular tension generated due to the movement of the muscles responsible for this bodily motion, and detects the supination of the forearm. For example, in the left upper limb, if the amount of rotation in the counterclockwise direction is greater than a predetermined value, then the controller 90 can determine that supination has been performed.

The explanation given above was about the types of bodily motion. In the state of an upper limb attained after performing one of the bodily motions, the muscle activity carried out to maintain that state is detectable as well as the muscle activity carried out either to perform the concerned bodily motion on a continuing basis or to again perform the concerned bodily motion in the concerned state is detectable.

Regarding the muscle activity carried out to maintain the state of the upper limb after a bodily motion has been performed; for example, after the clenching motion of a hand (fourth pattern) has been performed, there is muscle activity carried out to maintain the state in which the hand is clenched representing the state in which the first to fifth fingers are bent. In the following explanation, such muscle activity is referred to as state maintenance muscle activity.

From the state of the upper limb after a bodily motion has been performed, as the muscle activity carried out either to perform the concerned bodily motion on a continuing basis or to again perform the concerned bodily motion; for example, after the clenching motion of a hand (fourth pattern) has been performed and the hand is in the clenched state, there is muscle activity carried out at the time when the user intentionally exerts force for further attempting the clenching motion. At that time, the user clenches the hand by exerting stronger force than the state maintenance muscle activity carried out to maintain the state of the clenched hand. Because of such muscle activity, there is no change in the position/shape of the upper limb representing a displacement of the body. In the following explanation, such muscle activity is referred to as no-displacement muscle activity.

The state maintenance muscle activity does not occur at the time when the user intentionally performs a motion for performing an operation. For that reason, the configuration can be such that, when the state maintenance muscle activity is detected, the controller 90 does not instruct any predetermined operation based on the detection. The no-displacement muscle activity occurs at the time when the user intentionally performs a motion for performing an operation. For that reason, the configuration can be such that, when the no-displacement muscle activity is detected, the controller 90 instructs a predetermined operation based on the detection. Thus, the motion responsible for the no-displacement muscle activity is referred to as a "power motion" that is one of the "bodily motions (sometimes simply referred to as motions)" according to the embodiments.

Regarding distinctively detecting state maintenance muscle activity and no-displacement muscle activity, for example, if the muscular tension detected by the muscle activity detector 70 is smaller than a predetermined threshold value, then the controller 90 can determine that the muscle activity attributed to the bodily motion is state maintenance muscle activity. On the other hand, for example, if the muscular tension detected by the muscle activity detector 70 is greater than the predetermined threshold value, then the controller 90 either can determine that the muscle activity attributed to the bodily motion is no-displacement muscle activity or can determine that the bodily motion is a power motion. Moreover, regarding a power motion, the controller 90 can perform the determination as follows. Firstly, the controller 90 detects the bodily motion according to one of a plurality of patterns described earlier and, based on the type of that bodily motion, determines the state of the upper limb including the position/shape of the upper limb after the concerned bodily motion has been performed. Subsequently, when the next bodily motion is detected, if it is determined that the next bodily motion is not accompanied by a change in the state of the upper limb, the controller 90 can determine that the next bodily motion is a power motion.

In the bodily motion according to each pattern described earlier, the state of the upper limb representing the starting point of that bodily motion can be any state except for the states not attainable according to the bodily characteristics of a person. For example, in the case of detecting the palmar flexion of a hand (sixth pattern), the state in which the wrist is neither bent to the side of the flat of the hand nor bent to the side of the back of the hand is assumed to be a "neutral position", and the palmar flexion of the hand can be detected to have been performed in the following cases: (1) with the starting point represented by a state in which the wrist is bent by a predetermined angle to the side of the back of the hand, the motion of moving the wrist to the neutral position; (2) the motion of moving the wrist from the neutral position to the state of being bent to the side of the flat of the hand by a predetermined angle; and (3) with the starting point represented by a state in which the wrist is bent by a predetermined angle to the side of the back of the hand, the motion of moving the wrist to the state of being bent by a predetermined angle to the side of the flat of the hand. Depending on the state of the upper limb representing the starting point of a bodily motion or depending on the difference in the state of the upper limb immediately before performing a bodily motion, it can be determined whether or not the detection of the bodily motion is to be allowed. For example, in the case of detecting the palmar flexion of a hand (sixth pattern) as described above, it can be appropriately defined that the detection of the abovementioned case (1) as a palmar flexion is disallowed and that the detection of the abovementioned case (2) or (3) as a palmar flexion is allowed. In order to distinguish between the bodily motions having different starting points as in the cases (1), (2), and (3); the distinction can be made, for example, based on the difference in the frequency characteristic of myoelectric potential data according to the bodily motion, or based on the difference in the muscular tension, or based on the difference in the time of variation occurring in the muscular tension.

Meanwhile, the "neutral position" can be appropriately defined according to the type of bodily motion. Moreover, a bodily motion of moving to the neutral position from a state of the upper limb different than the neutral position can be set as a 12-th pattern.

Meanwhile, the controller 90 also detects a bodily motion formed by combining a plurality of bodily motions from among the first pattern to the 11-th pattern described earlier.

Figure 4A:
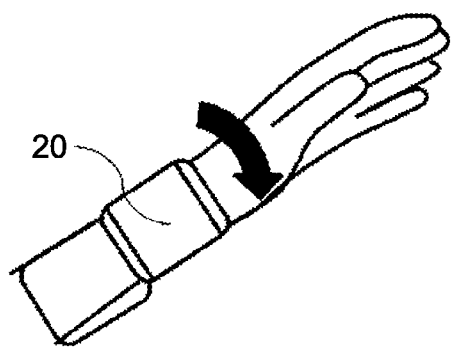
FIG. 4A is a diagram illustrating an example of a mode of the display operation performed by a display.
Figure 4B:
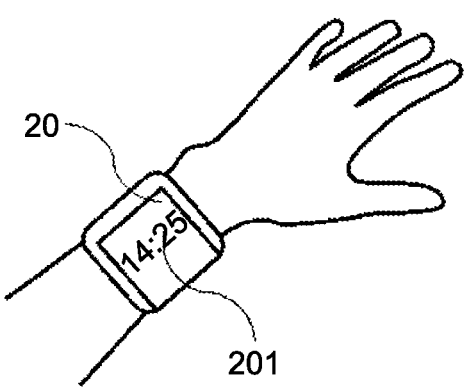
FIG. 4B is a diagram illustrating an example of the mode of the display operation performed by the display.

Given below is the explanation of a mode at the time of making the display 20 to perform a predetermined display operation as a predetermined operation in response to a bodily motion of the user. FIG. 4A is a diagram illustrating an example of a mode of the display operation performed by the display 20. FIG. 4B is a diagram illustrating an example of the mode of the display operation performed by the display. As illustrated in FIGS. 4A and 4B, for example, the wearable device 1 is strapped to the left upper limb representing one of the upper limbs of the user. With reference to FIG. 4A, on the near side of the page space is illustrated the lateral on the side of the radius of the forearm of the user. The display 20 has a display area also on the portion along the lateral of the forearm of the user. With regard to a state of FIG. 4A, for example, in the state in which the hand is unclenched, although the state maintenance muscle activity carried out for maintaining that state is detected by the controller 90, no other muscle activity is detected. Thus, a predetermined operation in response to the detection of muscle activity is not performed. The state illustrated in FIG. 4A is, for example, a state in which a hand unclenching motion is performed as an advance bodily motion but in which neither the state maintenance muscle activity for maintaining the state of the unclenched hand is detected nor any other bodily motion is detected. At that time, the user is intentionally not exerting force. Thus, a predetermined operation in response to the detection of muscular activity is not performed. Hence, no particular image is displayed on the display 20.

In such a state, if the user pronates the forearm; then the display 20 displays, for example, an image 201 containing information about the current time as the predetermined image as illustrated in FIG. 4B. With reference to FIG. 4B, as the state attained after the pronation of the forearm, on the near side of the page space is illustrated a portion that is present in the upper side of the forearm of the user and that is visible along with the back of the hand. In FIG. 4B, in the display area of the display 20, the predetermined image 201 is displayed at the position corresponding to the portion along the upper side of the forearm.

As a mode, the myoelectric potential detectors 71 detect the myoelectric potential generated as a result of the pronation of a forearm performed by the user. Based on that myoelectric potential, the controller 90 detects that the "pronation of a forearm (10-th pattern)" is actually performed. Then, based on the fact that the "pronation of a forearm (10-th pattern)" is performed, the controller 90 controls the display 20 to perform a display operation of displaying the predetermined image 201.

Meanwhile, the controller 90 can activate the wearable device 1 based on a predetermined bodily motion that has been detected and can notify the user about the activation of the wearable device 1, for example, by making a speaker that is optionally included in the wearable device 1 to output a predetermined sound, or by making a vibration device that is separately included in the wearable device 1 to output predetermined vibrations, or by illuminating in a predetermined manner a lighting device that is optionally included in the wearable device 1.

As described earlier, the wearable device 1 according to the embodiments is strapped to one upper limb from among the left and right upper limbs of the user. In the wearable device 1, the myoelectric potential detectors 71 detect myoelectric potential; and the controller 90 detects a bodily motion of the concerned upper limb based on the detected myoelectric potential, and instructs the display 20 to perform a predetermined display operation in response to the detected bodily motion. With such a configuration, in the wearable device 1 strapped to one upper limb from among the left and right upper limbs, operations can be performed in response to the motions of the concerned upper limb. As a result, as compared to conventional wearable devices, the wearable device 1 enables implementation of more diverse operations.

The wearable device 1 can perform operations without requiring a touch operation with respect to itself. For that reason, the wearable device 1 can prevent itself from getting dirty due to touch operations, thereby maintaining its aesthetic appearance as an accessory of the wristwatch type.

For example, if the user is wearing a wristwatch on a forearm and if the dial face of the wristwatch is positioned on the outer side of the forearm, then it is a perfectly natural bodily motion of the user to pronate the forearm so as to view the dial face. In that regard, in the wearable device 1 illustrated in FIGS. 4A and 4B, the controller 90 is configured to detect pronation of the forearm of the concerned upper limb as a bodily motion and to display a predetermined image in response to the detection of that bodily motion. As a result of having such a configuration, images useful to the user can be displayed along with the pronation of the forearm that is a perfectly natural bodily motion of the user to view the image displayed by the wearable device 1. For that reason, the user is spared from having to purposely perform extra operations or motions so as to view the desired images, thereby achieving enhancement in the operability of the wearable device 1.

As described earlier, pronation is a bodily motion for turning the forearm in such a way that the back of the hand faces the side of the face of the user. Thus, for the user who has performed pronation, it becomes easier to view the outer side of the forearm. For that reason, as illustrated in FIG. 4B, at the time of displaying the predetermined image 201 as the display operation along with the pronation, the wearable device 1 can be configured to display the predetermined image 201 in the display area that is in the portion of the display 20 along the outer side of the forearm and that is along the back of the hand of the forearm.

In this mode, the wearable device 1 is configured to perform a display operation based on the pronation of the forearm. However, that is not the only possible case. Alternatively, the wearable device 1 can be configured to perform a display operation based on the supination of the forearm.

The wearable device 1 can be configured to perform a display operation based on a rotation including the pronation and the supination. As described earlier, supination is a bodily motion for turning the forearm in such a way that the flat of the hand faces the side of the face of the user. With that, for the user who has performed supination, it becomes easier to view the inner side of the forearm along with the flat of the hand. For that reason, at the time of displaying a predetermined image as the display operation along with the supination, the wearable device 1 can be configured to display the predetermined image in the display area that is in the portion of the display 20 along the inner side of the forearm and that is along the flat of the hand of the forearm.

In the example explained above, with reference to FIG. 4A, either only the state maintenance muscle activity for maintaining the unclenched hand state is detected and no other muscle activity is detected, or not even the state maintenance muscle activity is detected. However, those are not the possible cases. Alternatively, with reference to FIG. 4A, it is possible to have a state in which some other bodily motion is performed for implementing a predetermined display operation. Even in the case in which, in continuation to the other bodily motion, a bodily motion to switch to the state illustrated in FIG. 4B is detected in succession, the display operation in response to that can be performed.

Figure 5A:
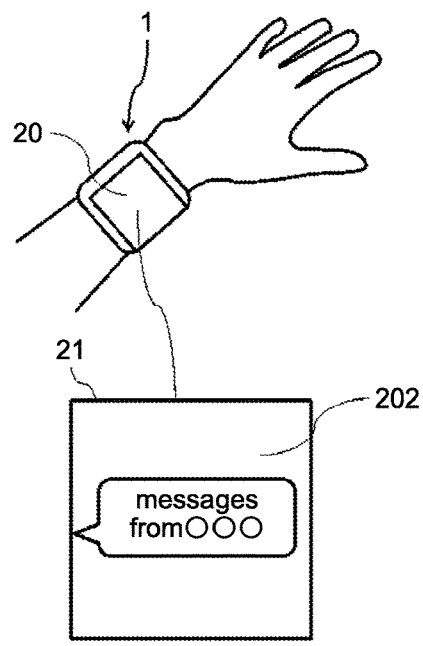
FIG. 5A is a diagram illustrating an example of another mode of the display operation performed by the display.
Figure 5B:
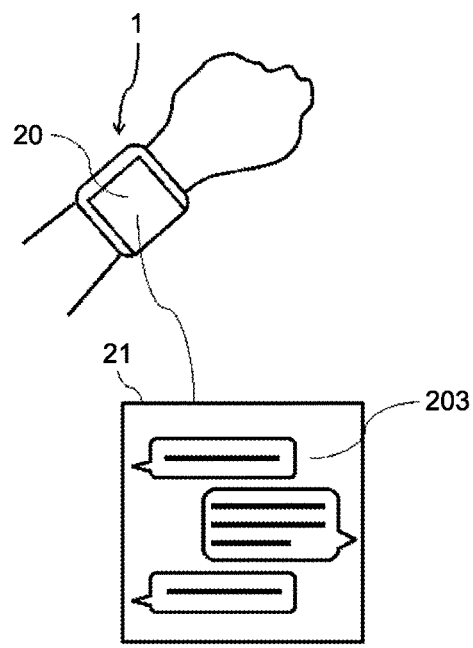
FIG. 5B is a diagram illustrating an example of the other mode of the display operation performed by the display.

Given below is the explanation of another mode at the time of making the display 20 to perform a predetermined display operation in response to a bodily motion of the user. FIG. 5A is a diagram illustrating an example of the other mode of the display operation performed by the display 20. FIG. 5B is a diagram illustrating an example of the other mode of the display operation performed by the display 20. In FIGS. 5A and 5B, in addition to illustrating the body part of the user to which the wearable device 1 is strapped, the display contents of the display 20 of the wearable device 1 are separately illustrated in an enlarged manner.

As illustrated in FIG. 5A, the wearable device 1 is strapped to, for example, one of the upper limbs of the user. At that time, the hand of the concerned upper limb of the user is in the unclenched state. In this state, in an identical manner to the earlier mode, either the state can be such that only the state maintenance muscle activity for maintaining the unclenched hand state is detected and no other muscle activity is detected, or the state can be such that not even the state maintenance muscle activity is detected. Regarding the other mode explained below, although the explanation is given about the control of a display operation in response to a predetermined bodily motion, it is assumed that the state before the detection of a bodily motion is identical to the earlier mode unless otherwise specified. In FIG. 5A, the display 20 displays a predetermined image in the display area corresponding to the upper side of the forearm. In this display area, as illustrated in FIG. 5A, for example, as the predetermined image, a first image 202 is displayed that is an image for reception notification representing a notification of receiving a message from a device such as a mobile device carried by another user. Herein, a message is received by the communication unit 40 by performing information communication. As a result of displaying the first image 202, the user can get to know about the message reception.

After viewing the first image 202, when the user switches to the hand clenching state as illustrated in FIG. 5B from the hand unclenching state and performs a bodily motion of clenching the hand, a second image 203 is displayed in place of the first image 202 on the display 20. The second image 203 is an image associated to the first image 202. For example, the second image 203 indicates the contents of the received message.

At that time, the myoelectric potential detectors 71 detect the myoelectric potential generated as a result of the hand clenching motion performed by the user. Based on that myoelectric potential, the controller 90 detects that the "clenching motion of a hand (fourth pattern)" is actually performed. Then, based on the fact that the "clenching motion of a hand (fourth pattern)" is performed, the controller 90 controls the display 20 to perform a display operation for switching the display from displaying the first image 202 to displaying the second image 203.

In this other mode, the explanation is given for an example in which, in response to the detection of a bodily motion of the user, the display is switched from displaying the first image 202 to displaying the second image 203. For example, in an identical manner to the earlier mode, in response to the detection of a bodily motion of the user, for example, the state such as the sleep state in which nothing is displayed is cancelled and, for example, switching is done to the state in which a predetermined image such as the first image 202 or the second image 203 is displayed.

As described above, in an identical manner to the earlier mode, the wearable device 1 in this other mode is strapped to one upper limb from among the left and right upper limbs of the user. In the wearable device 1, the myoelectric potential detectors 71 detect myoelectric potential. Based on the detected myoelectric potential, the controller 90 detects the bodily motion of the concerned upper limb, and instructs the display 20 to perform a predetermined display operation in response to the detected bodily motion. As a result of having such a configuration, in the wearable device 1 strapped to one upper limb from among the left and right upper limbs, operations can be performed in response to the motions of the concerned upper limb. As a result, as compared to conventional wearable devices, the wearable device 1 enables implementation of more diverse operations.

In the wearable device 1 according to this other mode, the controller 90 is configured to detect a motion of the hand of the concerned upper limb as a bodily motion. As a result of having such a configuration, without requiring the movement of the forearm to which the wearable device 1 is strapped, the wearable device 1 can instruct the display 20 to perform a predetermined display operation in response to a bodily motion of the hand. For that reason, in the wearable device 1, the position of the display 20 does not change during a bodily motion, thereby making it possible for the user to perform operations while visually confirming that a display operation has been performed by the display 20. In this way, the wearable device 1 enables achieving enhancement in the operability for the user.

In the wearable device 1 according to this other mode, the display 20 is made to perform a predetermined display operation in response to the detection of a clenching motion as a bodily motion of the hand. However, that is not the only possible case. Alternatively, for example, in the wearable device 1, the display 20 can be made to perform a predetermined display operation in response to the detection of a hand unclenching motion.

Figure 6A:
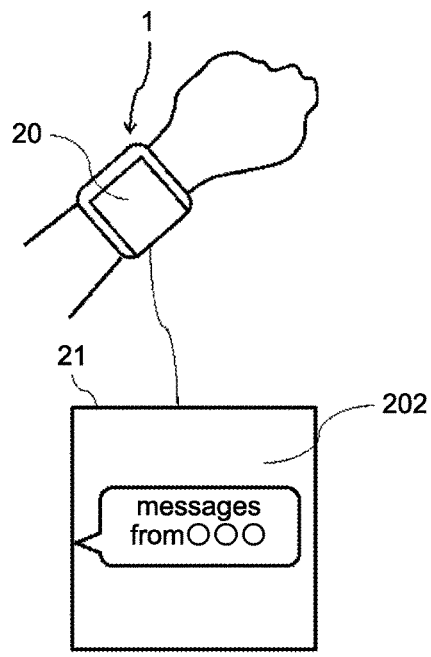
FIG. 6A is a diagram illustrating an example of another mode of the display operation performed by the display.
Figure 6B:
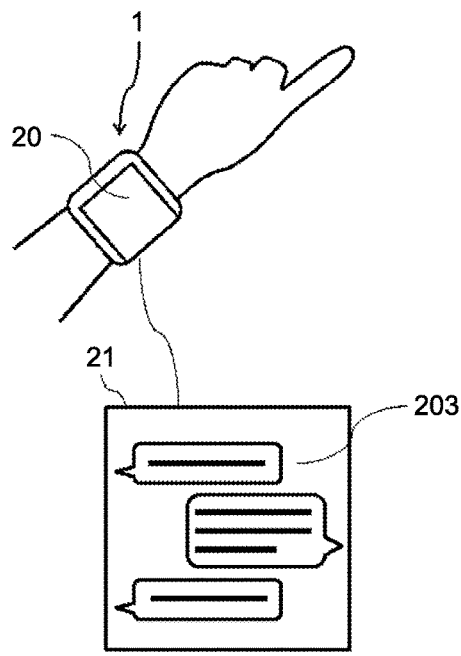
FIG. 6B is a diagram illustrating an example of the other mode of the display operation performed by the display.

Given below is the explanation of another mode at the time of making the display 20 to perform a predetermined display operation in response to a bodily motion of the user. FIG. 6A is a diagram illustrating an example of the other mode of the display operation performed by the display 20. FIG. 6B is a diagram illustrating an example of the other mode of the display operation performed by the display 20.

In FIGS. 6A and 6B too, in an identical manner to FIGS. 5A and 5B, in addition to illustrating the body part of the user to which the wearable device 1 is strapped, the display contents of the display 20 of the wearable device 1 are separately illustrated in an enlarged manner.

As illustrated in FIG. 6A, the wearable device 1 is strapped to, for example, one of the upper limbs of the user. At that time, the hand of the concerned upper limb of the user is in the clenched state. In the hand of the concerned upper limb of the user, all of the first to fifth fingers are in a bent state. The display 20 is displaying a predetermined image in the display area corresponding to the outer side of the forearm. In this display area, in an identical manner to the mode described earlier, the first image 202, which is an image for reception notification, is displayed as the predetermined image.

After viewing the first image 202, when the user switches to the state in which the second finger is extended as illustrated in FIG. 6B from the state in which all of the first to fifth fingers are bent and performs a motion of extending the second finger, the second image 203 is displayed in place of the first image 202 on the display 20. The second image 203 is an image associated with the first image 202. For example, the second image 203 indicates the contents of the received message.

At that time, the myoelectric potential detectors 71 detect the myoelectric potential generated as a result of the motion of extending the second finger as performed by the user. Based on that myoelectric potential, the controller 90 detects that the "extension motion of the second finger (second pattern)" is actually performed. Then, based on the fact that the "extension motion of the second finger (second pattern)" is performed, the controller 90 controls the display 20 to perform a display operation for switching the display from displaying the first image 202 to displaying the second image 203.

As described above, with regard to the wearable device 1 according to this other mode, in an identical manner to the modes described earlier, in the wearable device 1 strapped to one upper limb from among the left and right upper limbs, operations can be performed in response to the motions of the concerned upper limb. As a result, as compared to conventional wearable devices, the wearable device 1 enables implementation of more diverse operations.

In the wearable device 1 according to this other mode, the controller 90 is configured to detect a motion of a finger of the concerned upper limb as a bodily motion. As a result of having such a configuration, without requiring the movement of the forearm to which the wearable device 1 is strapped, the wearable device 1 can instruct the display 20 to perform a predetermined display operation in response to a bodily motion of a finger. For that reason, in the wearable device 1, the position of the display 20 does not change during a bodily motion, thereby making it possible for the user to perform operations while visually confirming that a display operation has been performed by the display 20. In this way, the wearable device 1 enables achieving enhancement in the operability for the user.

In the wearable device 1 according to this other mode, the display 20 is made to perform a predetermined display operation in response to the detection of an extension motion of a finger as a bodily motion of the hand. However, that is not the only possible case. Alternatively, for example, in the wearable device 1, the display 20 can be made to perform a predetermined display operation in response to the detection of a finger bending motion.

Figure 7A:
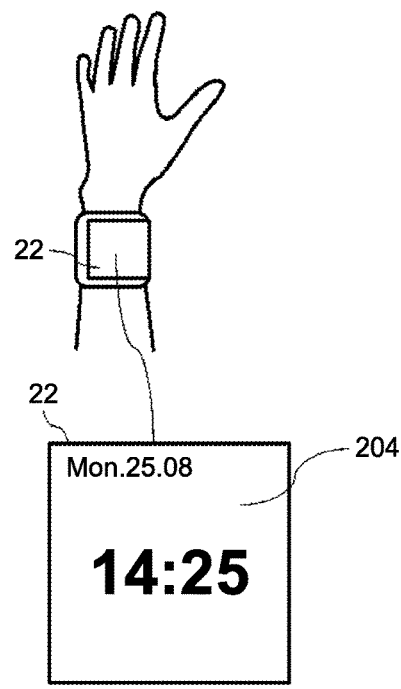
FIG. 7A is a diagram illustrating an example of another mode of the display operation performed by the display.
Figure 7B:
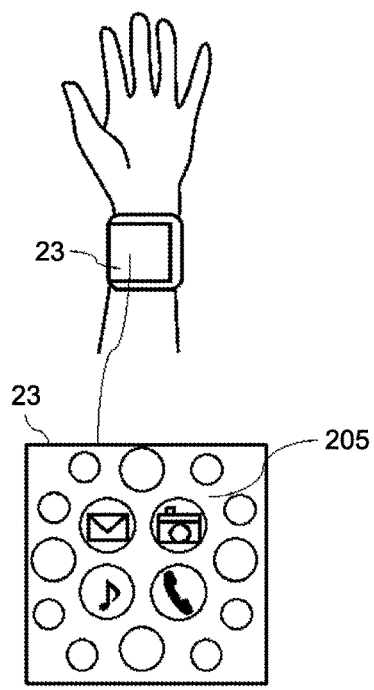
FIG. 7B is a diagram illustrating an example of the other mode of the display operation performed by the display.

Given below is the explanation of another mode at the time of making the display 20 to perform a predetermined display operation in response to a bodily motion of the user. FIG. 7A is a diagram illustrating an example of the other mode of the display operation performed by the display 20. FIG. 7B is a diagram illustrating an example of the other mode of the display operation performed by the display 20. In an identical manner to the modes described earlier, in this other mode, the display 20 is made to perform a predetermined display operation in response to the detection of rotation of a forearm as a bodily motion.

In FIG. 7A is illustrated the outer side of the forearm of the concerned upper limb of the user. In FIG. 7B is illustrated the inner side of the forearm of the concerned upper limb of the user. The display 20 includes a first display area 22 placed along the outer side portion of the forearm and a second display area 23 placed along the inner side portion of the forearm. The display 20 displays a different image in each display area. As illustrated in FIG. 7A, in the first display area 22 placed on the side of the back of the hand, for example, an image 204 containing information about the current time is displayed. As illustrated in FIG. 7B, in the second display area 23 placed on the side of the flat of the hand, for example, an image 205 is displayed that represents what is called a home screen in which various icons for executing various applications are displayed.

Typically, in the state of looking straight at the inner side of the forearm, it is impossible to look straight at the outer side of the forearm. In the state of looking straight at the outer side of the forearm, it is impossible to look straight at the inner side of the hand of the forearm. Thus, the first display area 22 corresponding to the outer side of the forearm and the second display area 23 corresponding to the inner side of the forearm cannot be simultaneously looked straight at. For that reason, if a predetermined image can be displayed in one display area, from among the first display area 22 and the second display area 23, that is being viewed by the user; then it becomes possible to hold down the unnecessary consumption of electrical power attributed to displaying an image in the other display area that is not being viewed by the user. Regarding which display area, from among the first display area 22 and the second display area 23, is being viewed by the user or which display area is in an easy-to-view state; the determination can be done, for example, according to whether pronation is performed or whether supination is performed as described earlier.

The wearable device 1 can be configured in such a way that, when the controller 90 detects pronation, a predetermined image is displayed in the first display area 22 as illustrated in FIG. 7A because it is considered that the outer side of the forearm is in an easy-to-view state. Similarly, the wearable device 1 can be configured in such a way that, when the controller 90 detects supination, a predetermined image is displayed in the second display area 23 as illustrated in FIG. 7B because it is considered that the inner side of the forearm is in an easy-to-view state.

In this way, in the wearable device 1 according to this other mode, in response to the detection of pronation by the controller 90, a predetermined image can be displayed in the display area being viewed by the user. Thus, the wearable device 1 enables achieving enhancement in the operability for the user. Moreover, the wearable device 1 can not only display a predetermined image in the display area being viewed by the user, but also avoid displaying an image in the other display area not being viewed by the user. Hence, the wearable device 1 enables achieving reduction in unnecessary consumption of electric power.

Figure 8A:
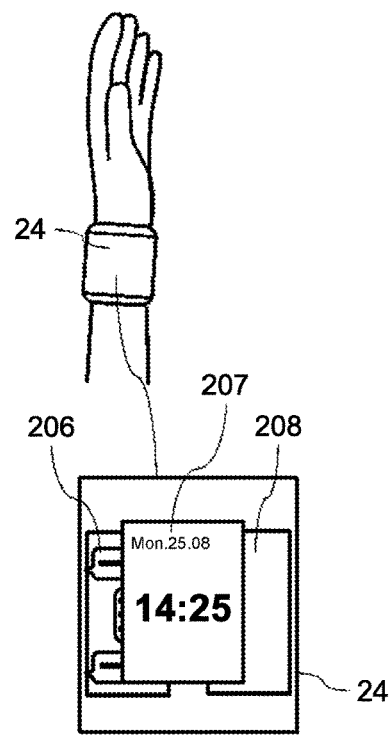
FIG. 8A is a diagram illustrating an example of another mode of the display operation performed by the display.
Figure 8B:
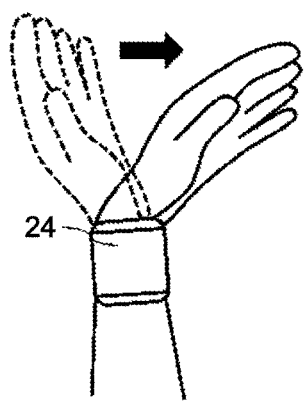
FIG. 8B is a diagram illustrating an example of the other mode of the display operation performed by the display.
Figure 8C:
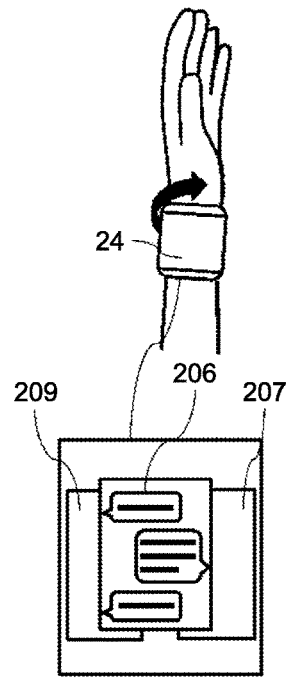
FIG. 8C is a diagram illustrating an example of the other mode of the display operation performed by the display.
Figure 8D:
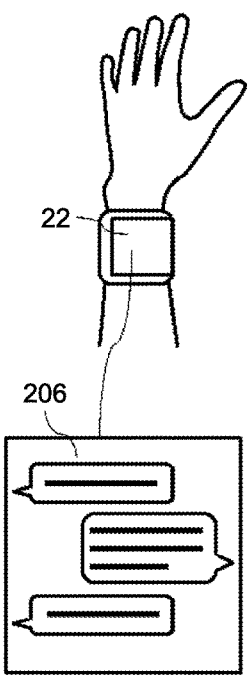
FIG. 8D is a diagram illustrating an example of the other mode of the display operation performed by the display.

Given below is the explanation of another mode at the time of making the display 20 to perform a predetermined display operation in response to a bodily motion of the user. FIG. 8A is a diagram illustrating an example of the other mode of the display operation performed by the display 20. FIG. 8B is a diagram illustrating an example of the other mode of the display operation performed by the display 20. FIG. 8C is a diagram illustrating an example of the other mode of the display operation performed by the display 20. FIG. 8D is a diagram illustrating an example of the other mode of the display operation performed by the display 20. In FIG. 8A is illustrated the lateral of the forearm of the upper limb to which the wearable device 1 is strapped. Herein, the lateral of the forearm on the side of the pollex of the concerned upper limb is illustrated. In the display 20, a third display area 24 is illustrated that is placed along the lateral of the forearm. The third display area 24 is an area placed in between the first display area 22, which corresponds to the outer side of the forearm, and the second display area 23, which is on the side of the flat of the hand corresponding to the inner side of the forearm. With reference to FIG. 8A, in the third display area 24, a plurality of display image candidates 206 to 208 is displayed.

The state in which the third display area 24 is placed along the lateral of the forearm as illustrated in FIG. 8A can be attained in the case in which, for example, supination is performed from the state in which the first display area 22 corresponding to the outer side of the forearm is easy to view as illustrated in FIG. 7A, but the supination is stopped midway while switching to the state in which the second display area 23 corresponding to the inner side of the forearm is easy to view as illustrated in FIG. 7B. Similarly, the state illustrated in FIG. 8A can be attained in the case in which pronation is performed from the state in which the second display area 23 corresponding to the inner side of the forearm is easy to view as illustrated in FIG. 7B, but the pronation is stopped midway while switching to the state in which the first display area 22 corresponding to the outer side of the forearm is easy to view as illustrated in FIG. 7A.

In that regard, at the time of detecting rotation of the forearm, the controller 90 calculates the amount of rotation and, if the amount of rotation is smaller than a predetermined value, determines that the state in which the third display area 24 placed along the lateral of the forearm is visible has been attained, as illustrated in FIG. 8A. According to such determination, the controller 90 controls the display 20 to substitute the first display area 22 or the second display area 23 with the third display area 24 and to display a predetermined image in the third display area 24.

In this way, in the wearable device 1 according to the other mode, as a result of having such a configuration, when it is deemed that the lateral of the forearm is being viewed instead of the outer side or the inner side of the forearm, an image can be displayed in the display area placed along the lateral. For that reason, the user is spared from having to purposely move the body in order to make the display easier to view. Thus, the wearable device 1 enables achieving enhancement in the operability for the user.

Returning to the explanation with reference to FIGS. 8A to 8D, in FIG. 8A, a plurality of display image candidates 206 to 208 is displayed in the third display area 24. The configuration is such that one of the display image candidates 206 to 208 becomes selectable in response to a predetermined operation of the user. For example, in FIG. 8A, it is illustrated that, from among the display image candidates 206 to 208, the display image candidate 207 positioned and displayed in the center has been selected.

For example, as illustrated in FIG. 8B, when the user performs palmar flexion as a bodily motion of the hand of the user, the mode of the display operation performed by the display 20 switches to the state illustrated in FIG. 8C. As described earlier, the palmar flexion illustrated in FIG. 8B is a bodily motion of bending the wrist to the side of the flat of the hand. As illustrated by an arrow in FIG. 8B, the palmar flexion is a motion of bending the wrist in the rightward direction. Along with the motion of bending the wrist in the rightward direction, the display image candidate 208 that is displayed on the rightmost side in FIG. 8A gets hidden in FIG. 8C. Moreover, along with the motion of bending the wrist in the rightward direction, the display image candidate 207, which is displayed in the center in FIG. 8A, and the display image candidate 206, which is displayed on the leftmost side in FIG. 8A, are displayed on the immediate right-hand side as illustrated in FIG. 8C. Then, the display image candidate 206, which is now displayed in the center, switches to the state of being selected in place of the display image candidate 207 that has moved to the rightmost side. Moreover, in the leftmost area in which the display image candidate 206 was displayed in FIG. 8A, a new display image candidate 209 gets displayed in FIG. 8C.

In this way, the wearable device 1 according to this other mode has such a configuration that, if a plurality of display image candidates is displayed in the display 20, when a predetermined bodily motion is detected, the controller 90 makes one of a plurality of display image candidates selectable in response to the bodily motion and displays the display image candidates by moving them in the same direction as the direction of motion of the bodily motion. Hence, the wearable device 1 enables selection of a display image candidate in response to a natural bodily motion of the user. In this way, the wearable device 1 enables achieving enhancement in the operability for the user.

Meanwhile, in the wearable device 1, based on the number of times for which the controller 90 detects a bodily motion, the mode of movement of the display image candidates can be changed. For example, as illustrated in FIGS. 8A and 8B, when the palmar flexion is detected once, the controller 90 moves a plurality of display image candidates by an amount equal to a single image. Moreover, in the wearable device 1, for example, when the palmar flexion is detected for a plurality of number of times, the controller 90 can move a plurality of display image candidates by an amount equal to a plurality of images.

Returning to the explanation with reference to FIGS. 8A to 8D, in the wearable device 1, along with palmar flexion representing the motion of bending the wrist in the rightward direction, each of a plurality of display image candidates is moved to the immediate right-hand side. Moreover, the wearable device 1 can be so configured that, when dorsal flexion is performed that represents the motion of bending the wrist in the leftward direction and that is the opposite motion of palmar flexion, each of a plurality of display image candidates is moved to the immediate left-hand side. In this way, the wearable device 1 can be so configured that a plurality of display image candidates are moved in opposite directions in response to palmar flexion and dorsal flexion.

With reference to FIG. 8C, in the wearable device 1, the display image candidate 206, such as a screen for displaying the communication of messages with another user, is displayed in the center and is in the selected state. In the wearable device 1, when the controller 90 detects pronation of the forearm, the display of other display image candidates is hidden and only the display image candidate 206 is displayed and determined to be selected as illustrated in FIG. 8D. When pronation is performed, the outer side of the forearm becomes easily viewable as described earlier. Thus, when pronation is performed, the first display area 22 placed along the outer side of the forearm becomes easily viewable. Hence, the selected display image candidate 206 can be displayed in the first display area 22 as illustrated in FIG. 8D.

In the wearable device 1 according to this other mode, the configuration is such that the display image candidate 206 is selected and displayed in the first display area 22 in response to pronation. However, that is not the only possible case. Alternatively, for example, the wearable device 1 can be configured in such a way that, when the controller 90 detects supination from the state illustrated in FIG. 8C, the display image candidate 206 is selected and displayed in the second display area 23.

In this other mode, the wearable device 1 is configured in such a way that, along with palmar flexion representing a first motion, each of a plurality of display image candidates is moved to the immediate right-hand side for display; and, along with dorsal flexion representing a second motion that is opposite to palmar flexion, each of a plurality of display image candidates is moved to the immediate left-hand side for display. Moreover, the wearable device 1 is so configured that the motion count of motions such as palmar flexion or dorsal flexion is calculated and counted, and the number of times of moving the display image candidates is varied according to the motion count. In that case, if the user performs the first motion for the first time and then attempts to perform the first motion for the second time, in order for the user to be able to again perform the first motion, he or she needs to once perform the second motion that is opposite to the first motion. That is, in this other mode, if the user performs palmar flexion for the first time and then attempts to perform palmar flexion for the second time, in order for the user to be able to again perform palmar flexion, he or she needs to once perform dorsal flexion. In that case, although the user wishes to move the display image candidates in a predetermined direction for a plurality of number of times by performing palmar flexion for a plurality of number of times; he or she ends up performing dorsal flexion, which is the opposite motion, in order to perform palmar flexion for a plurality of number of times. As a result, the display image candidates move in the opposite direction to the direction desired by the user.

In order to ensure that the state in which the first motion can be performed again is attained, the controller 90 can take the following measures for disallowing the detection of the second motion that is opposite to the first motion.

As the first measure, the controller 90 can be configured to disallow the detection of any second motion that is detected within a predetermined period of time since the detection of the first motion. Herein, regarding the second motion that is detected within a predetermined period of time since the detection of the first motion, the controller 90 can disallow the display operation performed by the display 20 in response to that second motion. In this other mode, for example, the controller 90 can be configured to disallow the detection of any dorsal flexion that is detected within a predetermined period of time since the detection of palmar flexion. For example, regarding any dorsal flexion that is detected within a predetermined period of time since the detection of palmar flexion, the controller 90 can disallow the display operation performed by the display 20 in response to that second motion. Herein, the predetermined period of time is set to 0.1 second, for example.

As another measure, the state that is attained in between the state in which the first motion is performed and the state in which the second motion is performed is detected as an "intermediate position"; and, after the initial first motion is detected, regarding the motion of switching to the "intermediate position" from the state in which the first motion is performed, the controller 90 can disallow the detection of the second motion. Moreover, with the state in which the first motion is performed serving as the starting point, regarding the motion of switching to the state in which the second motion is performed in the opposite manner to the first motion, the controller 90 can allow the detection of the second motion. Meanwhile, based on the state of the body immediately before the detection of a bodily motion, the controller 90 can vary the contents of the display operation. In this other mode, as described earlier, the state in which the wrist is neither bent to the side of the flat of the hand nor bent to the side of the back of the hand is assumed to be the "neutral position (intermediate position)". Thus, after the initial palmar flexion is detected, when the wrist is bent to the side of the flat of the hand by a predetermined angle, regarding the motion of switching to the "neutral position" from that state, the controller 90 can disallow the detection of dorsal flexion. Moreover, with the state in which the wrist is bent to the side of the flat of the hand by a predetermined angle serving as the starting point, regarding the motion of switching to the state in which the wrist is bent to the side of the back of the hand by a predetermined angle, the controller 90 can allow the detection of that motion as dorsal flexion.

As still another measure, the controller 90 can calculate a first time period spanning from the detection of the first motion to the detection of the second motion, can calculate a second time period spanning from the detection of the second motion to the detection of the first motion, and can allow the counting of the motion count of either the first motion or the second motion based on the first time period and the second time period. In this other mode, for example, the controller 90 can calculate a first time period spanning from the detection of palmar flexion to the detection of dorsal flexion, can calculate a second time period spanning from the detection of dorsal flexion to the detection of palmar flexion, and can allow the counting of the motion count of either palmar flexion or dorsal flexion based on the first time period and the second time period.

For example, if the first time period is shorter than the second time period, it can be considered that the user is ready to perform palmar flexion as the next motion. For that reason, the controller 90 can allow the counting of the motion count of palmar flexion. On the other hand, if the second time period is shorter than the first time period, it can be considered that the user is ready to perform dorsal flexion as the next motion. For that reason, the controller 90 can allow the counting of the motion count of dorsal flexion.

Figure 9A:
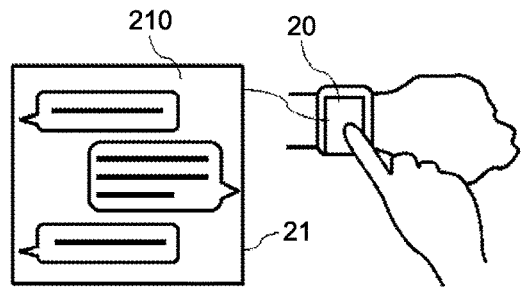
FIG. 9A is a diagram illustrating an example of another mode of the display operation performed by the display.
Figure 9B:
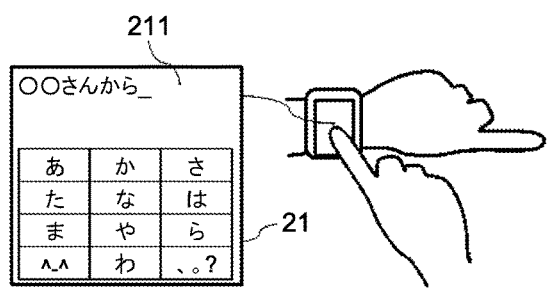
FIG. 9B is a diagram illustrating an example of the other mode of the display operation performed by the display.
Figure 9C:
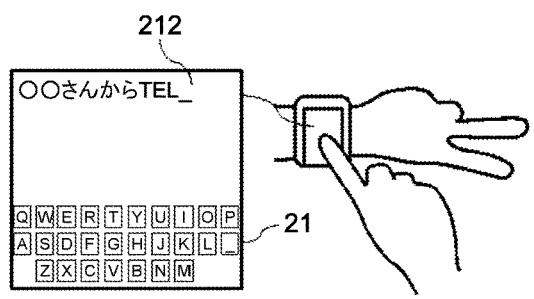
FIG. 9C is a diagram illustrating an example of the other mode of the display operation performed by the display.
Figure 9D:
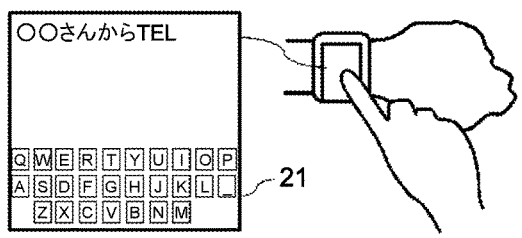
FIG. 9D is a diagram illustrating an example of the other mode of the display operation performed by the display.

Given below is the explanation of another mode at the time of making the display 20 to perform a predetermined display operation in response to a bodily motion of the user. FIG. 9A is a diagram illustrating an example of the other mode of the display operation performed by the display 20. FIG. 9B is a diagram illustrating an example of the other mode of the display operation performed by the display 20. FIG. 9C is a diagram illustrating an example of the other mode of the display operation performed by the display 20. FIG. 9D is a diagram illustrating an example of the other mode of the display operation performed by the display 20.

In this other mode, in the wearable device 1, a touch sensor representing the touch operation unit 30 is disposed in an overlapping manner with the display 20. Thus, in the wearable device 1, a touch operation can be performed on the screen displayed on the display 20. In FIG. 9A is illustrated a state in which, with respect to the image displayed on the display 20 of the wearable device 1 strapped to the forearm, a touch operation can be performed using the right upper limb representing the other upper limb.

With reference to FIG. 9A, the hand of the concerned upper limb of the user has all of the first to fifth fingers in the bent state. In a display area 21 of the display 20, for example, a screen 210 for displaying the communication of messages with another user is displayed. If the controller 90 detects, for example, the "the extension motion of the second finger (second pattern)" as the first bodily motion from among the bodily motions, then the display 20 displays a character entry screen 211 representing a first touch-operation reception screen as illustrated in FIG. 9B. The character entry screen 211 representing the first touch-operation reception screen is meant for entering kana characters.

Then, in the state illustrated in FIG. 9B, if the controller 90 detects, for example, the "the extension motion of the third finger (second pattern)" as the second bodily motion from among the bodily motions, then the display 20 displays a character entry screen 212 representing a second touch-operation reception screen. The character entry screen 212 representing the second touch-operation reception screen is meant for entering alphabets.

Herein, the explanation is given about an example in which, at the time of switching from the state illustrated in FIG. 9B to the state illustrated in FIG. 9C, the third finger is extended while maintaining the extended state of the second finger illustrated in FIG. 9B. However, that is not the only possible case. Alternatively, in the wearable device 1, for example, at the time of switching from the state illustrated in FIG. 9B to the state illustrated in FIG. 9C, even if the second finger is released from the extended state and if the third finger is extended while bending the second finger, that bodily motion can be allowed to be detected.

The wearable device 1 can be configured in such a way that the first touch-operation reception screen can be continuously displayed since the detection of the first bodily motion till the detection of another bodily motion, and that the second touch-operation reception screen can be continuously displayed since the detection of the second bodily motion till the detection of another bodily motion.

Subsequently, in FIG. 9C is illustrated a state in which "OO san kara TEL_ (TEL from Mr. OO_)" that is input in Japanese language by the user is displayed in the display area 21 along with an underscore indicating the readiness to receive the next character entry. If the controller 90 detects the "clenching motion of a hand (fourth pattern)" as the third motion from among the bodily motions, then the display 20 completes the character entry and switches the display to the state in which the underscore is no more displayed as illustrated in FIG. 9D.

For example, when the wearable device 1 includes the touch operation unit 30, it is a difficult task to perform a touch operation on the touch operation unit 30 using a finger of the upper limb to which the wearable device 1 is strapped. Hence, the operations on the touch operation unit 30 are usually performed using the other upper limb on the opposite side of the upper limb to which the wearable device 1 is strapped.

In that regard, the wearable device 1 according to this other mode is configured in such a way that, unlike with the detection of a touch operation, a predetermined operation is detected based on the myoelectric potential generated due to a bodily motion of the upper limb to which the wearable device 1 is strapped. For that reason, the wearable device 1 can perform operations in response to the motions of the fingers of the concerned upper limb. As a result, as compared to the conventional case in which the myoelectric-potential-based detection of an operation is not performed, the wearable device 1 enables implementation of more diverse operations.

In the other mode, the explanation is given for an example in which the "extension motion of the second finger" is performed as the first bodily motion and the "extension motion of the third finger" is performed as the second bodily motion. Herein, each of the first and second bodily motions can be performed using any finger of the first to fifth fingers. Moreover, each motion is not limited to be the extension motion of a finger, but can alternatively be the motion of bending a finger that is in the extended state. Still alternatively, each motion can be a pinching motion between the first finger and one of the second to fifth fingers. Still alternatively, each motion is not limited to be a motion of a finger, and any individually-detectible motion of the hand or the forearm can be used.

According to the characteristics of the bodily tissues of a person, the muscles responsible for a bodily motion of the first to fifth fingers are identical as described earlier. Particularly, it is a difficult task to separate the signals transmitted to the muscles for moving the little finger from the signals transmitted to the muscles for moving the ring finger. For that reason, it may often happen that the little finger and the ring finger get simultaneously bent or extended.

Thus, when the abovementioned first motion is the motion of a particular finger and when the abovementioned second motion is the motion of another finger of the concerned upper limb, it can be ensured that the little finger and the ring finger are not respectively assigned for the first motion and the second motion. If either the little finger or the ring finger represents the particular finger, then a finger other than the ring finger and the little finger can be assigned as the other finger.

Figure 10A:
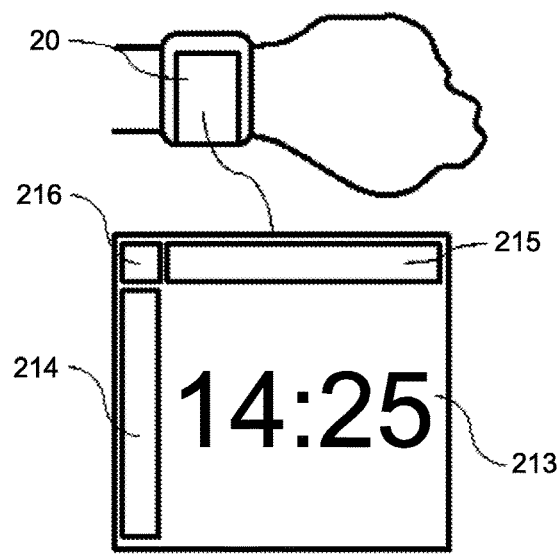
FIG. 10A is a diagram illustrating an example of another mode of the display operation performed by the display.
Figure 10B:
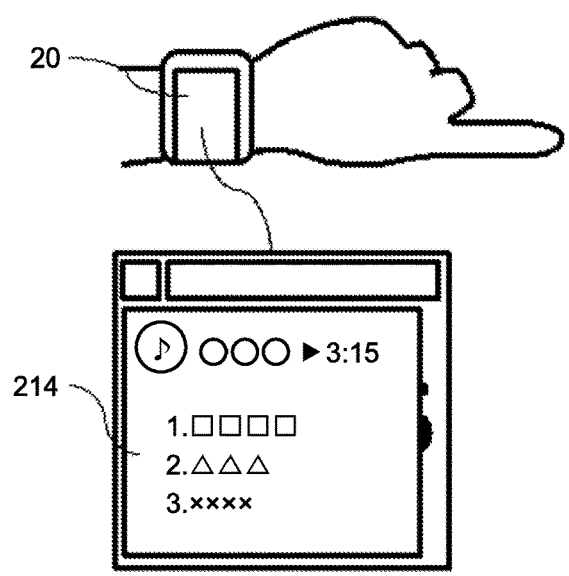
FIG. 10B is a diagram illustrating an example of the other mode of the display operation performed by the display.
Figure 10C:
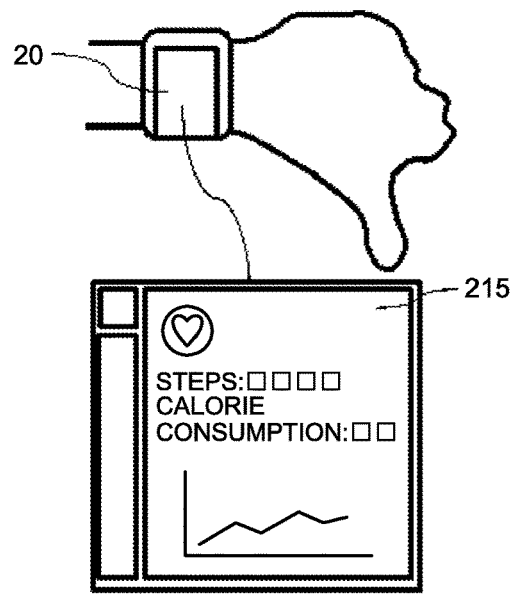
FIG. 10C is a diagram illustrating an example of the other mode of the display operation performed by the display.
Figure 10D:
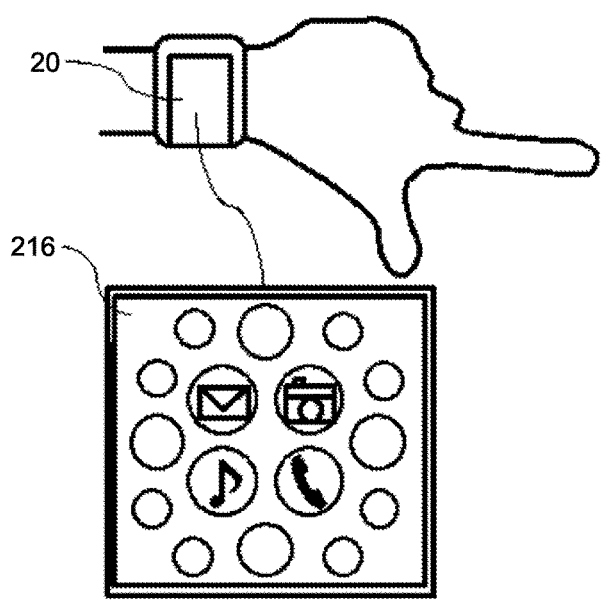
FIG. 10D is a diagram illustrating an example of the other mode of the display operation performed by the display.

Given below is the explanation of another mode at the time of making the display 20 to perform a predetermined display operation in response to a bodily motion of the user. FIG. 10A is a diagram illustrating an example of the other mode of the display operation performed by the display 20. FIG. 10B is a diagram illustrating an example of the other mode of the display operation performed by the display 20. FIG. 10C is a diagram illustrating an example of the other mode of the display operation performed by the display 20. FIG. 10D is a diagram illustrating an example of the other mode of the display operation performed by the display 20. As illustrated in FIG. 10A, the wearable device 1 is strapped to one upper limb of the user and all fingers of that upper limb are in the bent state. In the entire display area 21 of the display 20, an image 213 containing information about the date and time is displayed. In an end-portion area close to the left-hand edge of the display area 21, an image 214 is displayed in an overlapping manner with the image 213. Similarly, in an end-portion area close to the upper-hand edge of the display area 21, an image 215 is displayed in an overlapping manner with the image 213. In the top left corner of the display area 21, an image 216 is displayed in an overlapping manner with the image 213.

If the controller 90 detects the extension motion of, for example, the second finger representing one of the second to fifth fingers, then the image 214 that is displayed in the end-portion area close to the left-hand edge of the display area 21 gets displayed in an enlarged manner in the rightward direction representing the direction of extension of the second finger, as illustrated in FIG. 10. The image 214 which has been displayed in an enlarged manner is, for example, an image containing operation items related to a music playback application. Herein, the image 214 which has been displayed in an enlarged manner can be subjected to operations including a touch operation using the other upper limb on the opposite side of the upper limb to which the wearable device 1 is strapped. In the image 214 which has not been displayed in an enlarged manner, for example, information, such as the song title being currently played, that is smaller in volume than the volume of information displayed in the image 214 which has been displayed in an enlarged manner can be displayed.

Along with detecting the extension motion of the second finger, the controller 90 can be configured to vary the enlargement ratio of the image 214 based on the amount of extension or the amount of bending of the second finger. For example, as the second finger goes on extending or as the amount of bending goes on decreasing, the controller 90 can display the image 214 in a more enlarged manner. Herein, the amount of bending of a finger implies the angle of bending of each joint of the finger.

In the state of enlarged display of the image 214 as illustrated in FIG. 10B, if the controller 90 detects the bending motion of the second finger, the display can be returned to the state illustrated in FIG. 10A.

Subsequently, in the state illustrated in FIG. 10A, when the controller 90 detects the extension motion of the first finger, the image 215 that is displayed in the end-portion area close to the lower edge of the display area 21 is displayed in an enlarged manner in the downward direction representing the direction of extension of the first finger as illustrated in FIG. 10C. The image 215 which has been displayed in an enlarged manner contains, for example, a variety of information related to a health monitoring application. The image 215 which has been displayed in an enlarged manner can be subjected to operations including a touch operation using the other upper limb on the opposite side of the upper limb to which the wearable device 1 is strapped. In the image 215 which has not been displayed in an enlarged manner, for example, information, such as the number of steps taken, that is smaller in volume than the volume of information displayed in the image 215 which has been displayed in an enlarged manner can be displayed.

Along with detecting the extension motion of the first finger, the controller 90 can be configured to vary the enlargement ratio of the image 214 based on the amount of extension or the amount of bending of the first finger. For example, as the first finger goes on extending or as the amount of bending goes on decreasing, the controller 90 can display the image 215 in a more enlarged manner.

In the state of enlarged display of the image 215 as illustrated in FIG. 10C, if the controller 90 detects the bending motion of the first finger, the display can be returned to the state illustrated in FIG. 10A.

In the state in which the second finger is extended as illustrated in FIG. 10B, if the controller 90 detects the extension motion of the first finger, then the image 215 can be displayed in an enlarged manner as illustrated in FIG. 10C. At that time, the image 215 gets displayed in an overlapping manner with the image 214.

Subsequently, in the state illustrated in FIG. 10A, if the controller 90 detects the extension motion of one finger, such as the second finger from among the second to fifth fingers, as well as detects the extension motion of the first finger at the same time, then the image 216 that is displayed in the top left corner of the display area 21 gets displayed in an enlarged manner in the rightward direction representing the direction of extension of the second finger and in the downward direction representing the direction of extension of the first finger, as illustrated in FIG. 10D. The image 216 which has been displayed in an enlarged manner represents what is called a home screen in which various icons for executing various applications are displayed.

In this way, the wearable device 1 according to this other mode varies the image to be displayed depending on the different fingers that perform an extension motion. That is, the wearable device 1 varies the image to be displayed depending on the different fingers that perform a bodily motion. With such a configuration, in response to the bodily motions of the upper limb to which the wearable device 1 is strapped, the wearable device 1 enables the user to confirm more diverse information.

Herein, the configuration can be such that, in the state in which the extension motion of fingers is not performed as illustrated in FIG. 10A, the images 214 to 216 are not displayed; and, when the extension motion of a finger is detected, one of the images 214 to 216 is displayed in a newly-inserted manner. At that time, it can be ensured that the direction of extension of the finger representing the direction of the bodily motion is consistent with the direction of insertion of one of the images 214 to 216. Moreover, the size of insertion of the images 214 to 216 can be varied according to the amount of extension of the finger.

Figure 11A:
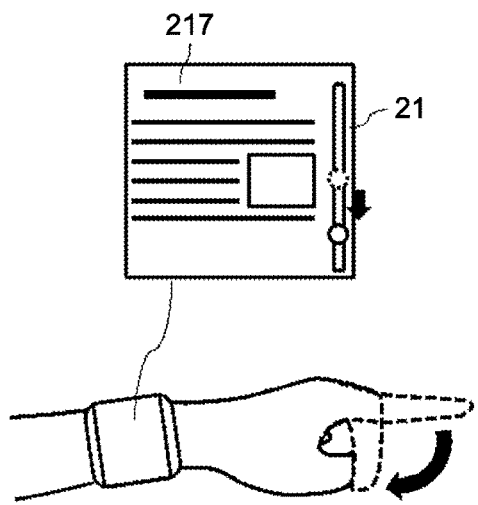
FIG. 11A is a diagram illustrating an example of another mode of the display operation performed by the display.
Figure 11B:
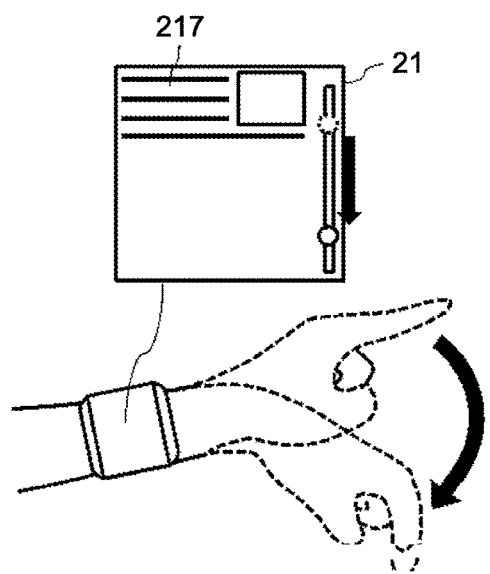
FIG. 11B is a diagram illustrating an example of the other mode of the display operation performed by the display.

Given below is the explanation of another mode at the time of making the display 20 to perform a predetermined display operation in response to a bodily motion of the user. FIG. 11A is a diagram illustrating an example of the other mode of the display operation performed by the display 20. FIG. 11B is a diagram illustrating an example of the other mode of the display operation performed by the display 20. In FIGS. 11A and 11B, the display contents that are displayed on the display area 21, which is present in the display 20 of the wearable device 1 and on the side of the back of the hand, are separately displayed in an enlarged and schematic manner.

In this other mode, as a predetermined bodily motion, the explanation is given for an example in which scrolling is performed using the bending motion and the extension motion representing bodily motions of a finger and an example in which scrolling is performed using palmar flexion and dorsal flexion representing bodily motions of a hand. The scrolling represents an operation in which, when the display contents cannot fit within the display area, only some portion of the display contents is displayed and the display contents are moved as necessary.

As illustrated in FIGS. 11A and 11B, in the display area 21, for example, a variety of information is displayed that is viewable upon the execution of a web browser application. In the display area 21, a scroll bar is displayed along the right-side edge. The scroll bar is a bar for indicating which portion of the overall display contents is being displayed.

As illustrated in FIGS. 11A and 11B, for example, if at least either a motion, such as palmar flexion, of the hand of the upper limb to which the wearable device 1 is strapped is detected as the predetermined bodily motion or a motion, such as a bending motion, of a finger of the concerned upper limb is detected as the predetermined bodily motion; scrolling is performed in response to that bodily motion. At that time, the controller 90 can calculate, for example, the amount of bending of the finger or the amount of bending of the wrist and, based on the calculated amount of bending, vary the amount of movement of the image representing the amount of scrolling. In the wearable device 1, the controller 90 can be configured to calculate the amount of displacement of the body along with a bodily motion of the concerned upper limb and, as the display operation performed by the display 20, vary the display contents based on the calculated amount of displacement. With such a configuration, the wearable device 1 enables implementation of diverse operations with a single bodily motion.

As illustrated in FIG. 11A, in the wearable device 1, for example, if the controller 90 detects that the bending motion of a finger is performed without palmar flexion, then the display contents are scrolled by a first amount of movement. As illustrated in FIG. 11B, in the wearable device 1, for example, if the controller 90 detects that the bending motion of a finger is performed along with palmar flexion, then the display contents are scrolled by a second amount of movement that is greater than the first amount of movement. Alternatively, in the wearable device 1, for example, if the controller 90 detects that the bending motion of a finger is performed without palmar flexion, then the display contents are scrolled at a first speed of movement. As illustrated in FIG. 11B, in the wearable device 1, for example, if the controller 90 detects that the bending motion of a finger is performed along with palmar flexion, then the display contents are scrolled at a second speed of movement that is faster than the first speed of movement.

In this way, in the wearable device 1 according to this other mode, when either a motion of the hand or a motion of a finger is detected, the controller 90 makes the display 20 to perform a first display operation; and, when a motion of the hand as well as a motion of a finger is detected, the controller 90 makes the display 20 to perform a second display operation. As a result of having such a configuration of the wearable device 1 according to this other mode, regarding a motion having a combination of a plurality of bodily motions, it is possible to assign a display operation that is different from the display operations based on individual bodily motions. Thus, the wearable device 1 enables implementation of more diverse operations.

As described above, in the wearable device 1 according to this other mode, the second amount of movement, by which a predetermined image is moved in the second display operation in response to the detection of a motion of the hand as well as a motion of a finger, can be set to be greater than the first amount of movement, by which a predetermined image is moved in the first display operation in response to the detection of either a motion of the hand or a motion of a finger. As a result, by performing a bigger bodily motion, the predetermined image can be scrolled by a greater amount of movement. Thus, the wearable device 1 enables achieving enhancement in the user-friendliness.

In an identical manner, in the wearable device 1 according to this other mode, the second speed of movement, at which a predetermined image is moved in the second display operation in response to the detection of a motion of the hand as well as a motion of a finger, can be set to be greater than the first speed of movement, at which a predetermined image is moved in the first display operation in response to the detection of either a motion of the hand or a motion of a finger. As a result, by performing a bigger bodily motion, the predetermined image can be scrolled at a faster speed of movement. Thus, the wearable device 1 enables achieving enhancement in the user-friendliness.

In the example explained above, the controller 90 detects palmar flexion of the hand and a bending motion of a finger as predetermined bodily motions. In an identical manner, the controller 90 can also detect dorsal flexion of the hand and an extension motion of a finger. In that case, the direction of scrolling in response to dorsal flexion of the hand and an extension motion of a finger can be set to be opposite to the direction of scrolling in response to palmar flexion of the hand and a bending motion of a finger. For example, during the scrolling of a predetermined image in response to a bending motion of a finger or in response to a bending motion of fingers along with palmar flexion of the hand, if the controller 90 detects an extension motion of a finger or detects an extension motion of a finger along with dorsal flexion of the hand, then the scrolling can be stopped midway.

In the example explained above, the configuration is such that the amount of scrolling of display contents is varied based on the amount of displacement of the body during a bodily motion. However, that is not the only possible case. For example, the configuration of the wearable device 1 can be such that an object enabling making changes in a predetermined parameter, such as a sound volume adjustment bar displayed during the running of a music playback application or a seek bar displayed for indicating the position of playback of the data during the running of a movie playback application, is displayed and the predetermined parameter is changed in response to a bodily motion. In the wearable device 1, for example, during the running of the music playback application, the sound volume adjustment bar is operated in response to a bodily motion of a finger. For example, the configuration can be such that, when a finger is extended, the sound volume is raised according to the amount of extension or the amount of displacement and, when a finger is bent, the sound volume is lowered according to the amount of bending or the amount of displacement.

In the state in which the fingers of the upper limb are bent, in order to perform a sound volume adjustment operations, an extension operation of a finger needs to be performed once. In that case, in spite of no such intention of the user, the sound volume increases on its own thereby possibly causing a sense of discomfort to the user. In view of such a situation, in the wearable device 1 according to this other mode, for example, the state in between the state of completely-bent fingers and the predetermined state of completely-extended fingers is detected as an intermediate state and, when the bent state of the fingers changes to the intermediate state due to a bodily motion, the calculation of the amount of bending or the amount of extension, which represents the amount of displacement along with the bodily motion of the fingers, can be started. In the wearable device 1, the controller 90 can be configured to detect a predetermined intermediate state in between the state in which the first motion is performed and the state in which the second motion opposite to the first motion is performed and, when the state of the body becomes the intermediate state due to a bodily motion, to start calculating the amount of displacement of the body. As a result of having such a configuration of the wearable device 1, when the fingers of the upper limb are in the bent state, even if the extension motion of the fingers needs to be performed once in order to perform a sound volume adjustment operation, it can be ensured that the sound volume is not adjusted until the bent state of the fingers reaches the intermediate state. As a result, for example, the wearable device 1 can avoid a situation in which the sound volume is wrongly adjusted thereby causing a sense of discomfort to the user.

In this other mode, in the wearable device 1, with the abovementioned intermediate state serving as the reference state, the amount of displacement of the body from the reference state can be calculated as the amount of displacement of the body due to a bodily motion. In the example explained above, the controller 90 can detect the change in the amount of bending of the fingers and can calculate, as the amount of displacement of the body, the amount that has changed with respect to the amount of bending of the fingers in the intermediate state.

The amount of displacement of the body, such as the amount of bending of fingers, along with a bodily motion can be calculated according to the method of estimating the angles of joints of the fingers as disclosed in Japanese Patent Application Laid-open No. 2010-125287 A.

Figure 12A:
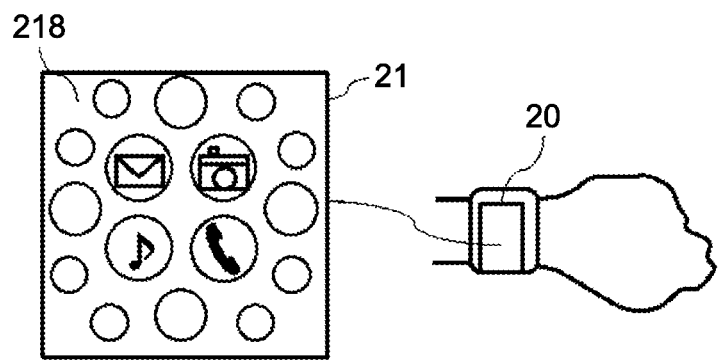
FIG. 12A is a diagram illustrating an example of another mode of the display operation performed by the display.
Figure 12B:
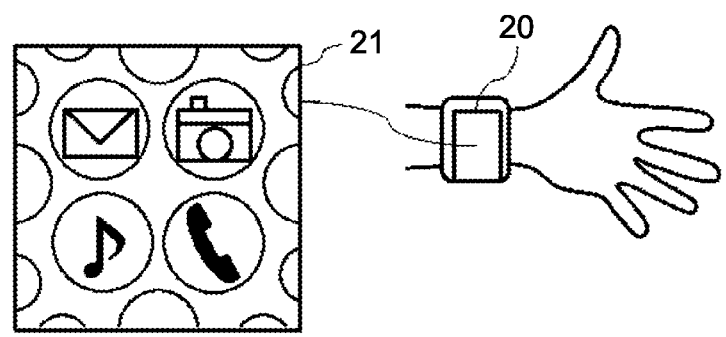
FIG. 12B is a diagram illustrating an example of the other mode of the display operation performed by the display.

In the mode illustrated in FIGS. 11A and 11B, the wearable device 1 is so configured that a parameter is changed in response to a bodily motion. However, that is not the only possible case. The explanation of other modes is given below. FIG. 12A is a diagram illustrating an example of the other mode of the display operation performed by the display 20. FIG. 12B is a diagram illustrating an example of the other mode of the display operation performed by the display 20.

In FIG. 12A, it is illustrated that an image 218, which represents what is called a home screen in which various icons for executing various applications are displayed, is displayed in the display area 21 of the display 20. Herein, the upper limb to which the wearable device 1 is strapped has the hand in a clenched state. If a hand unclenching motion is detected as a predetermined bodily motion, then the image 218 gets displayed in an enlarged manner as illustrated in FIG. 12B.

At that time, the controller 90 can calculate the amount of displacement representing the amount of hand unclenching at the time of switching from the state of clenched hand to the state of unclenched hand; vary the enlargement ratio of the image 218 based on the calculated amount of displacement; and accordingly vary the display contents. When it is detected that the state of unclenched hand has changed to the state of clenched hand, the controller 90 can reduce the image 218 according to the amount of bending of each finger.

In this way, in the wearable device 1 according to this other mode, a predetermined image is displayed in an enlarged manner in response to a bodily motion of the concerned upper limb of the user. As a result of having such a configuration, for example, at the time of performing a touch operation using the other upper limb of the user with the wearable device 1, it becomes easier for the user to touch the desired object in the predetermined image.

When an image is displayed in an enlarged manner, some of the display contents of the original image are displayed while the other display contents do not get displayed. Thus, the other display contents that do not get displayed can be displayed by moving them using scrolling, for example. In that case, since enlargement and reduction of the images is performed in response to a hand unclenching motion and a hand clenching motion or in response to an extension motion of a finger or a bending motion of a finger, the bodily motion for performing scrolling can be a bending motion of the wrist such as palmar flexion, dorsal flexion, radial flexion, or ulnar flexion.

Herein, although the embodiments are described with reference to the accompanying drawings, the present disclosure is not to be thus limited but is to be construed as embodying all modifications and alternative constructions that may occur to one skilled in the art that fairly fall within the basic teaching herein set forth. Moreover, all of the technical matter disclosed in the present written description can be rearranged without causing contradictions. That is, a plurality of constituent elements can be combined into a single constituent element or can be divided into more constituent elements.

The controller 90 can be configured to detect a power motion of the concerned upper limb and, if a bodily motion is detected within a predetermined period of time since the detection of the power motion, to allow the detection of that bodily motion; but, if a bodily motion is detected after a predetermined period of time since the detection of the power motion, to disallow the detection of that bodily motion.

The "power motion" mentioned above is usually hard to occur as a result of a motion not intended by the user. Thus, unless the user performs a "power motion", it is hard to be detected by the wearable device 1. Hence, regarding performing a predetermined operation in response to a bodily motion of the upper limb of the user, a bodily motion performed intentionally by the user is demanded as the condition for actually accepting the operation. With that, a situation can be prevented in which the wearable device 1 is mistakenly operated in response to a motion not intended by the user. Meanwhile, in place of the "power motion", it is possible to implement some other bodily motion that is hard to be detected unless performed intentionally by the user. As such a bodily motion, it is possible to use a pinching motion, such as a pinching motion between the first finger and one of the second to fifth fingers (third pattern).

In the case in which a predetermined motion is to be set or a predetermined operation is to be performed in response to an extension motion of a finger, instead of detecting a motion in which the finger is simply extended as the extension motion, an extension motion of the finger along with a flicking motion of the finger can be detected as the extension motion. Herein, examples of the "flicking motion of a finger" include a motion in which, in the state in which a predetermined finger from among the second to fifth fingers is bent, force is exerted so as to extend the predetermined finger and at the same time the predetermined finger is pressed from the outer side by the first finger so that a state of suppressing the extension motion is attained; and then the first finger is pulled away so that the predetermined finger is extended toward the outer side with force. When the predetermined finger is pressed by the first finger, the muscle activity occurring based on the opposing force applied mutually by the predetermined finger and the first finger can be detected by the muscle activity detector 70 and the controller 90, so that the motion can be detected as a "flicking motion of a finger". In this way, in the wearable device 1 according to the embodiments, the controller 90 can be configured to detect an opposing motion of the concerned upper limb with respect to some other object and, if a bodily motion is detected within a predetermined period of time since the detection of the opposing motion, to allow for performing the predetermined display operation; but, if a bodily motion is detected after a predetermined period of time since the detection of the opposing motion, to disallow for performing the predetermined display operation.

Figure 13:
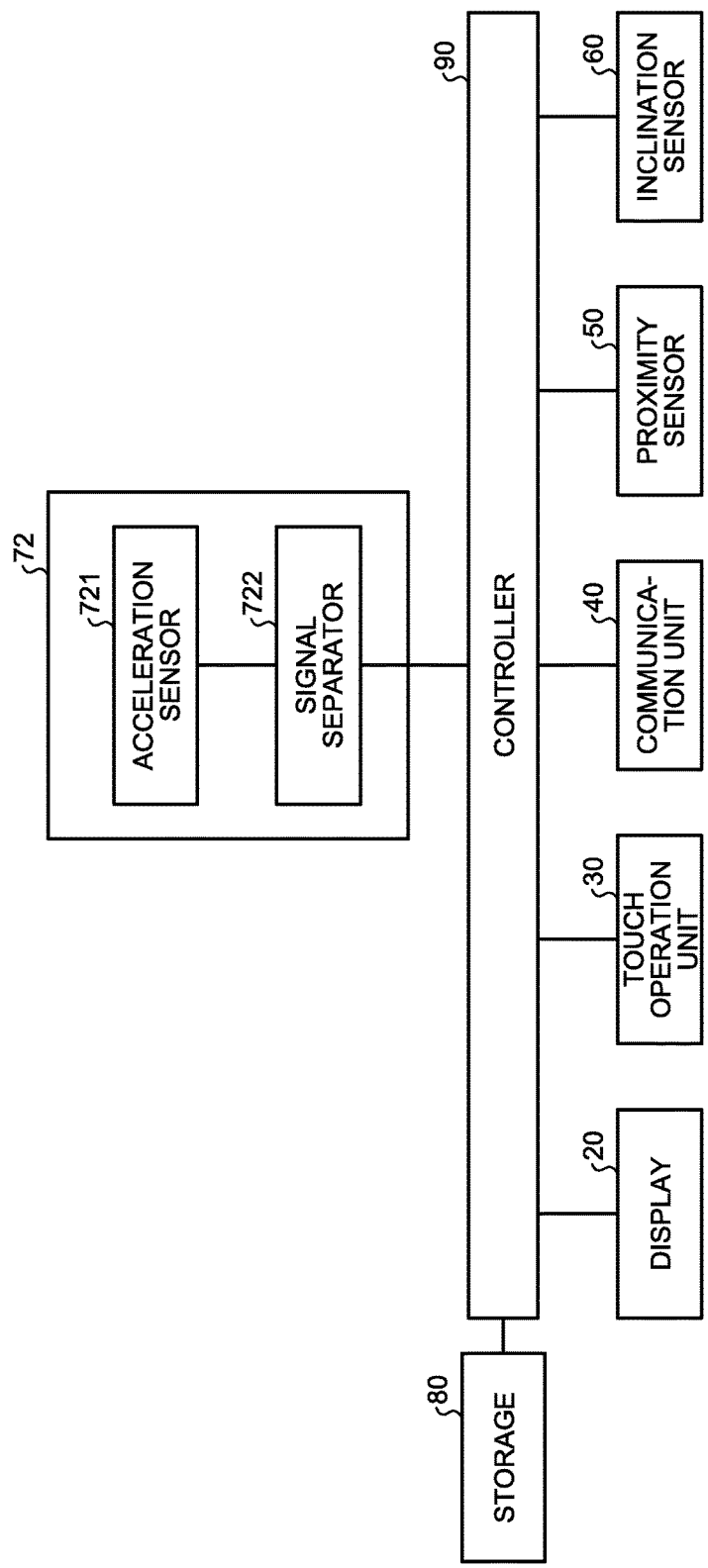
FIG. 13 is a diagram illustrating an example of the functional blocks of the wearable device in the case in which a muscle activity detector is represented by a muscle sound detector.

In the embodiments, the explanation is given for a case in which the muscle activity detector 70 is represented by the myoelectric potential detectors 71. However, instead of being represented by the myoelectric potential detectors 71, the muscle activity detector 70 can be represented by a muscle sound detector 72 that detects the minute vibrations generated at the time of muscle contraction as the muscle activity. The minute vibrations represent lateral enlarged deformation attributed to the contraction of muscle fibers. Regarding the minute vibrations, a form of pressure waves generated due to the deformation is detected as muscle sound signals. FIG. 13 is a diagram illustrating an example of the functional blocks of the wearable device in the case in which the muscle activity detector 70 is represented by the muscle sound detector 72. Herein, the display 20, the touch operation unit 30, the communication unit 40, the proximity sensor 50, the inclination sensor 60, and the storage 80 illustrated in FIG. 13 are identical to the functional blocks illustrated in FIG. 2. Hence, their explanation is not repeated.

The muscle activity detector 70 represents the muscle sound detector 72. Moreover, the muscle sound detector 72 includes an acceleration sensor 721 and a signal separator 722.

The acceleration sensor 721 is installed at a position that comes in contact with the concerned upper limb of the user. The acceleration sensor 721 detects signals corresponding to bodily motions of the user. The acceleration sensor 721 includes a single triaxial acceleration sensor and three single-axis acceleration sensors. The acceleration sensor 721 detects, as the signals mentioned above, signals including acceleration signals and muscle sound signals attributed to bodily motions of the upper limb. The acceleration signals are obtained from the X axis, the Y axis, and Z axis of the triaxial acceleration sensor. The muscle sound signals are obtained from a total of four channels including the Z axis of the triaxial acceleration sensor and the three single-axis acceleration sensors. The acceleration sensor 721 outputs signals including a detected acceleration signal and a detected muscle sound signal to the signal separator 722.

The signal separator 722 separates the muscle sound signal from the signals detected by the acceleration sensor 721. In a muscle sound signal generated at the time of muscle contraction, the frequency components are in the range of 5 Hz to 100 Hz. Hence, the signal separator 722 can separate the muscle sound signal using a filter in the range of 5 Hz to 150 Hz. The separated muscle sound signal is subjected to appropriate processing such as rectification, smoothing, and normalization; and is obtained as a characteristic pattern vector. The controller 90 determines the type of bodily motion from the characteristic pattern vector using, for example, a neural network.

Meanwhile, instead of obtaining a characteristic pattern vector from the muscle sound signal and then determining the bodily motion, the controller 90 can obtain a characteristic pattern vector from the acceleration signal and then determine the bodily motion. In that case, in order to separate the acceleration signal from the signals detected by the acceleration sensor 721, the signal separator 722 can perform separation using a filter in the range of 1 Hz to 3 Hz, for example.

In the case of determining the bodily motion from the acceleration signal, the configuration can be such that the muscular tension at the time of the bodily motion is detected from the muscle sound signal. At that time, the configuration can be such that, when the detected muscular tension exceeds a predetermined threshold value, the abovementioned power motion is detected.

As described above, in an identical manner to the myoelectric potential detectors 71, in the muscle sound detector 72 too, it is possible to determine the type of bodily motion of the user. Hence, the controller 90 becomes able to separately detect the motions of various patterns illustrated in FIG. 3. Thus, the wearable device 1 can perform a variety of display control in response to the bodily motions of the user as described above.

Meanwhile, the muscle sound detector 72 is not limited to include the abovementioned acceleration sensor, and can alternatively use other devices such as a capacitor microphone or a pressure sensor having a piezoelectric element.

The muscle activity detector 70 can be configured to perform myoelectric detection as well as muscle sound detection, and to obtain information about the muscle activity in a more accurate manner based on the correlation between the information obtained in the two types of detection.

In the embodiments, the explanation is given for a case in which the wearable device 1 is of the wristband type or the wristwatch type that is strapped close to the wrist of a forearm of the user. However, the form of the wearable device 1 is not limited to that example. Alternatively, for example, the wearable device 1 can be of the armband type that is strapped close to the elbow of a forearm of the user. Still alternatively, for example, if the requirement is to detect the bodily motions of the fingers, the wearable device 1 can be circular in shape that can be wrapped around the back of the hand and the flat of the hand at a position close to the bases of the four fingers, namely, the index finger to the fourth finger of the user. In the case of having the circular wearable device 1, for example, the myoelectric potential detectors 71 representing the muscle activity detector 70 can be installed in the wearable device 1 in such a way that they come in contact with the muscles close to the flat of the hand, such as the adductor muscle of thumb, the short flexor muscle of thumb, the opposer muscle of little finger, the short flexor muscle of little finger, and the abductor muscle of little finger that are responsible for the motions of the fingers.

In the modes described above, the explanation is given for a configuration in which the display contents are varied based on the amount of displacement of the body due to a bodily motion. However, that is not the only possible case. Alternatively, for example, the controller 90 can be configured to calculate the motion count of the bodily motions of the concerned upper limb and vary the display contents based on the motion count.

For example, based on the state of the fingers immediately before the detection of a bodily motion, it is possible to vary the display contents of a display operation to be performed in response to that bodily motion. For example, with reference to the example illustrated in FIG. 11B, in the state in which one finger from among the first to fifth fingers is extended representing the state of the fingers immediately before the detection of a bodily motion, if palmar flexion is detected, then a predetermined image can be moved by a first amount of movement. On the other hand, in the state in which two fingers from among the first to fifth fingers are extended representing the state of the fingers immediately before the detection of a bodily motion, if palmar flexion is detected, then a predetermined image can be moved by a second amount of movement that is greater than the first amount of movement. At that time, in the state of the fingers immediately before the detection of a bodily motion, greater the number of extended fingers, greater can be the amount of movement or faster can be the speed of movement of a predetermined image in response to the detection of palmar flexion.

Figure 14:
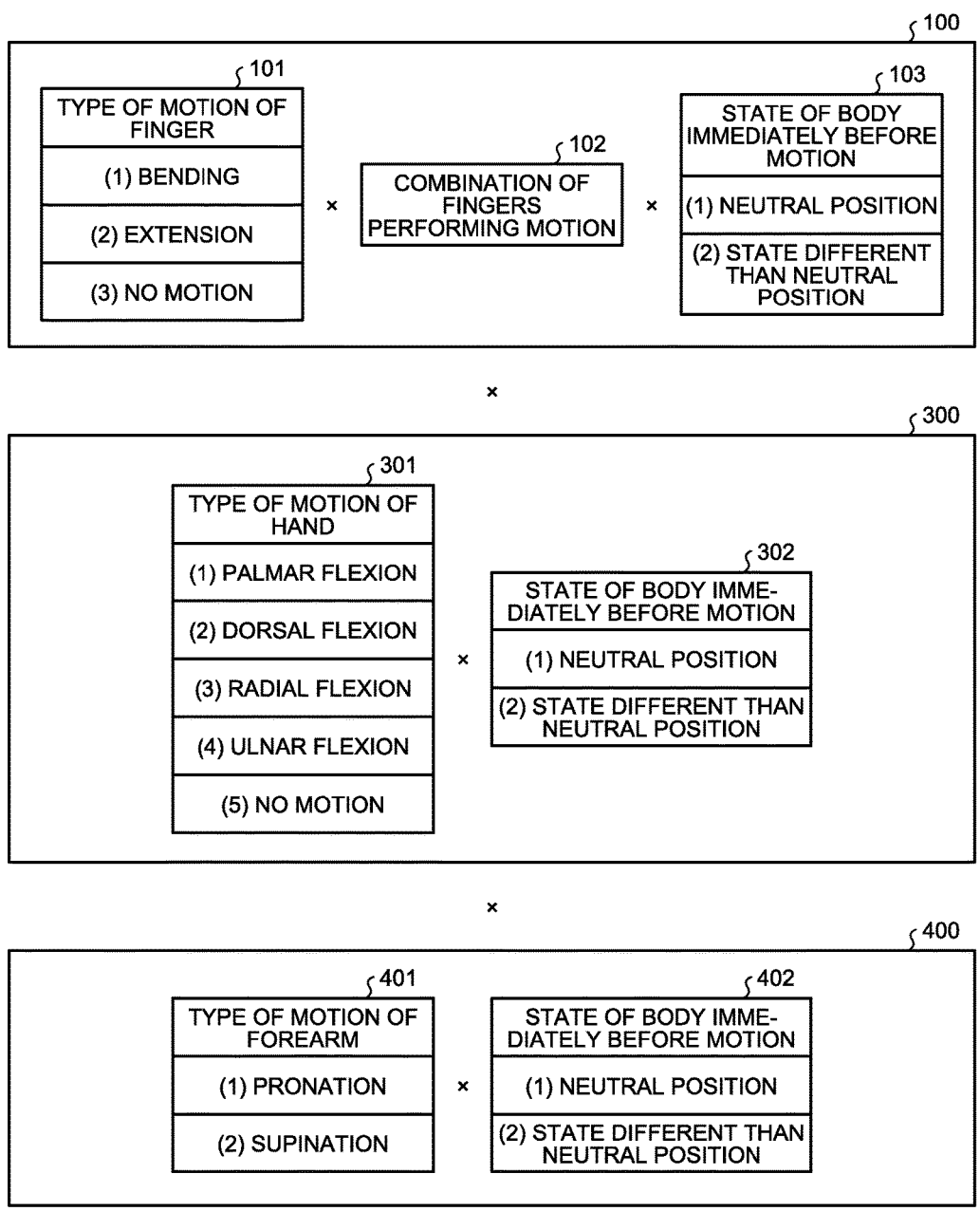
FIG. 14 is a diagram illustrating an exemplary table of elements characterizing bodily motions.

From a table of elements characterizing bodily motions as illustrated in FIG. 14, with respect to each motion in which bodily motions in the lists of categories are combined in such a way that the combination does not result in bodily motions that cannot be performed according to the bodily characteristics of a person, a different display operation can be associated. In the table of the elements characterizing bodily motions as illustrated in FIG. 14, a bodily motion including at least either a motion of fingers, or a motion of the hand, or a rotational motion of the forearm is combined with the state of the body immediately before the detection of that bodily motion. Firstly, in a broad category 100 related to the bodily motions of fingers, an element is selected from each of narrow categories 101 to 103, and the combination thereof results in defining the characteristic of the motion of fingers. In the narrow category 102, although elements are not illustrated, it implies that a combination of the fingers performing a motion is also selected as an element. In a broad category 300 related to bodily motions of the hand, an element is selected from each of narrow categories 301 and 302, and the combination thereof results in defining the characteristic of the motion of the hand or the wrist. In a broad category 400 related to bodily motions of the forearm, an element is selected from each of narrow categories 401 and 402, and the combination thereof results in defining the characteristic of the motion of the forearm. Then, with respect to bodily motions in which the motion of fingers characterized in the broad category 100, the motion of the hand characterized in the broad category 300, and the motion of the forearm characterized in the broad category 400 are performed either at the same time or in a sequential manner in random order; each bodily motion can be detected as a different bodily motion and a different display operation can be performed based on the detection.

In the embodiments, the explanation is given for a configuration in which the touch operation unit 30 is used to receive an operation performed by the other upper limb opposite to the upper limb to which the wearable device 1 is strapped. However, the functional unit for receiving an operation is not limited to the touch operation unit 30. Alternatively, for example, when the proximity sensor 50 detects that a finger of the other upper limb of the user either has come close or has moved away, the display 20 can be made to perform a predetermined display operation.

In the case of having a configuration in which the touch operation unit 30 is used to receive an operation performed by the other upper limb in an identical manner to the embodiments, for example, when the proximity sensor 50 detects that a finger of the other upper limb has come close to the touch operation unit 30, the display direction of the image displayed by the display 20 can be changed in such a way that the crosswise direction of the image is consistent with the long side of the arm.

For example, in the case of using a finger of the right upper limb to perform an operation on the touch sensor representing the touch operation unit 30 of the wearable device 1 that is strapped to the forearm of the left upper limb, the long side of the left forearm roughly intersects with the direction of extension of any finger of the right arm according to the bodily characteristics of a person. For that reason, if the image is displayed in such a way that the crosswise direction of the image is consistent with the long side of the arm, in other words, if the image is displayed in such a way that the vertical direction of the image is consistent with the short direction of the left forearm in which the radius and the ulna are lined; then the vertical direction of the image becomes consistent with the direction of extension of the fingers of the right hand used for performing operations. Thus, the wearable device 1 enables achieving enhancement in the operability.

In the case of having a configuration in which the touch operation unit 30 is used to receive an operation performed by the other upper limb in an identical manner to the embodiments, when the touch operation unit 30 receives a touch of a finger of the other upper limb, the shape of the touched portion can be detected, and accordingly the direction in which the finger extends and in which the base and the tip of the finger are lined can be determined; and the display direction of the image can be changed in such a way that the direction of extension of the finger is consistent with the vertical direction of the image.

In the case in which the aim is to establish communication between the wearable device 1 and the automatic ticket gate of a railway station and to go through the automatic ticket gate as explained in the embodiments, when the wearable device 1 strapped to the forearm of an upper limb is held over the information reader of the automatic ticket gate, the communication with the automatic ticket gate can be allowed in response to the detection of a predetermined bodily motion. For example, at the time of holding over the wearable device 1 from the side of the information reader of the automatic ticket gate, it is believed that the outer side of the forearm is held over and palmar flexion is performed so that the hand does not collide with the information reader at the time of holding over the forearm. Thus, when palmar flexion of the hand is detected as the predetermined bodily motion, the communication with the automatic ticket gate can be allowed.

Other than the example of the usage at an automatic ticket gate, for example, in the case of wanting to perform electronic payment using electronic money, it is also possible to think of a case in future in which the wearable device 1 is strapped to a forearm and is held over an information reading device meant for performing electronic payment. In such a case, at the time of holding over the wearable device 1 from above the information reading device, it is believed that the inner side of the forearm is held over and dorsal flexion is performed so that the hand does not collide with the information reader at the time of holding over the forearm. Thus, when dorsal flexion of the hand is detected as the predetermined bodily motion, the communication with the information reading device can be allowed.

Meanwhile, the configuration can be such that, at the time when the muscle activity detector 70 detects a bodily motion of the user, if the inclination sensor 60 has detected fluctuation of the wearable device 1, then the control by the controller 90 for making the display 20 to perform a display operation is disallowed. At the time when the muscle activity detector 70 detects a bodily motion of the user, if the inclination sensor 60 has not detected any fluctuation of the wearable device 1, then the control by the controller 90 for making the display 20 to perform a display operation is allowed.

If the inclination sensor 60 detects a state in which the display surface of the display 20 is inclined with respect to the horizontal plane by an angle much larger than a predetermined angle, then the control for making the display 20 to perform a display operation in response to the bodily motion can be disallowed. If the inclination sensor 60 detects a state in which the display surface of the display 20 is inclined with respect to the horizontal plane by an angle smaller than the predetermined angle, then the control for making the display 20 to perform a display operation in response to the bodily motion can be allowed.

Meanwhile, in the wearable device 1 according to the embodiments, the wearable device 1 can be assumed to include the display 20 that displays images; the detecting unit 70 for detecting a motion of such a bodily part, with the exception of the bodily part to which the wearable device 1 is attached, which cannot make contact with the wearable device 1; and the controller 90 that makes the display to perform a predetermined display operation in response to the detected bodily motion.

The invention claimed is:

1. A wearable device that is attached to one upper limb from among left and right upper limbs of a user, the wearable device comprising:
    a display configured to display an image;
    a muscle activity detector coming in contact with the one upper limb, the muscle activity detector configured to detect muscle activity of the one upper limb; and
    a controller configured to:
    detect a bodily motion of the one upper limb based on the detected muscle activity,
    cause the display to perform a predetermined display operation in response to the bodily motion
    calculate an amount of displacement of a body accompanying the bodily motion, and
    as the predetermined display operation, vary display contents of the display based on the amount of displacement,
    detect a predetermined intermediate state in between a state in which the first motion is performed and a state in which the second motion is performed,
    start calculating the amount of displacement when a state of the body reaches the intermediate state during the bodily motion with the intermediate state serving as a reference state, amount of displacement of the body from the reference state is calculated as the amount of displacement,
    detect a motion of fingers as the bodily motion,
    detect, as the intermediate state, a state in between a state in which fingers are completely bent and a state in which fingers are completely extended, and
    calculate, as the amount of displacement, amount of change by which amount of bending of the fingers changes with respect to amount of bending of fingers in the intermediate state.

2. A wearable device that is attached to one upper limb from among left and right upper limbs of a user, the wearable device comprising:
    a display configured to display an image;
    a muscle activity detector coming in contact with the one upper limb, the muscle activity detector configured to detect muscle activity of the one upper limb; and
    a controller configured to detect a bodily motion of the one upper limb based on the detected muscle activity, and configured to cause the display to perform a predetermined display operation in response to the bodily motion, wherein
    the display has a first display area placed along an outer side of the forearm and has a second display area placed along an inner side of the forearm,
    the display is placed along a forearm of the one upper limb,
    the controller is configured to detect a rotation motion of the forearm of the one upper limb as the bodily motion,
    the controller is configured to detect a pronation motion and a supination motion as the rotation motion,
    when the pronation motion is detected, the controller is configured to ensure that the predetermined image is displayed in the first display area as the predetermined display operation, and
    when the supination motion is detected, the controller is configured to ensure that the predetermined image is displayed in the second display area as the predetermined display operation.

3. The wearable device according to claim 2, wherein the display further has a third display area that
    is placed along lateral of the arm of the one upper limb, lateral corresponding to side of pollex of the upper limb, and
    is placed in between the first display area and the second display area,
    the controller is configured to calculate amount of rotation of forearm during the rotation motion, and
    when the amount of rotation is smaller than a predetermined value, the controller is configured to display the predetermined image in the third display area in place of the first display area or the second display area.

4. The wearable device according to claim 3, wherein
    in case of displaying the predetermined image in the third display area, the controller is configured to display a plurality of display image candidates in the third display area, and
    in response to the detected bodily motion, the controller is configured to make one of the plurality of display image candidates selectable.

5. The wearable device according to claim 4, wherein, in a state in which one of the plurality of display image candidates is selected, upon detecting the rotation motion, the display is configured to display the selected display image candidate in the first display area or the second display area as the predetermined display operation.

* * * * *